(12) United States Patent
Thieberger et al.

(10) Patent No.: US 12,282,598 B2
(45) Date of Patent: Apr. 22, 2025

(54) EFFICIENT IMAGE CAPTURING BASED ON EYELID POSITION

(71) Applicant: Facense Ltd., Kiryat Tivon (IL)

(72) Inventors: Gil Thieberger, Kiryat Tivon (IL); Ari M Frank, Haifa (IL)

(73) Assignee: Facense Ltd., Kiryat Tivon (IL)

( * ) Notice: Subject to any disclaimer, the term of this patent is extended or adjusted under 35 U.S.C. 154(b) by 11 days.

(21) Appl. No.: 18/473,232

(22) Filed: Sep. 23, 2023

(65) Prior Publication Data
US 2024/0012478 A1 Jan. 11, 2024

Related U.S. Application Data

(63) Continuation of application No. 17/490,432, filed on Sep. 30, 2021, now Pat. No. 11,803,237.
(Continued)

(51) Int. Cl.
*G06F 3/01* (2006.01)
*A61B 5/00* (2006.01)
(Continued)

(52) U.S. Cl.
CPC ............ *G06F 3/013* (2013.01); *A61B 5/0205* (2013.01); *A61B 5/02427* (2013.01); *A61B 5/02438* (2013.01); *A61B 5/14546* (2013.01); *A61B 5/1455* (2013.01); *A61B 5/6803* (2013.01); *G06V 10/141* (2022.01); *G06V 40/166* (2022.01); *G06V 40/174* (2022.01); *H04N 23/611* (2023.01); *H04N 23/651* (2023.01);
(Continued)

(58) Field of Classification Search
None
See application file for complete search history.

(56) References Cited

U.S. PATENT DOCUMENTS 6,542,081 B2 4/2003 Torch
7,515,054 B2 4/2009 Torch
(Continued)

FOREIGN PATENT DOCUMENTS

WO    WO2019067731    4/2019

OTHER PUBLICATIONS

Abdulin, Evgeniy R., and Oleg V. Komogortsev. "Study of Additional Eye-Related Features for Future Eye-Tracking Techniques." *Proceedings of the 2017 CHI Conference Extended Abstracts on Human Factors in Computing Systems.* 2017.
(Continued)

*Primary Examiner* — Talha M Nawaz
(74) *Attorney, Agent, or Firm* — Active Knowledge Ltd.

(57) ABSTRACT

Systems, methods, and computer programs for eye tracking involving a camera that is operated according to eyelid position. In one embodiment, an inward-facing head-mounted camera captures images of an eye. A head-mounted device emits electromagnetic waves towards the eye and measures reflections of these waves from the eye. The average rate of reflection measurements is at least ten times the average rate of image capture. A computer detects the position of at least one of the eyelids covering the eye based on the reflection measurements. And the camera operation is adjusted according to the eyelid position in a manner that decreases, in the captured images, areas depicting the eyelids, and optionally increases areas depicting the iris.

20 Claims, 7 Drawing Sheets

Related U.S. Application Data

(60) Provisional application No. 63/140,453, filed on Jan. 22, 2021, provisional application No. 63/122,961, filed on Dec. 9, 2020, provisional application No. 63/113,846, filed on Nov. 14, 2020.

(51) Int. Cl.
```
A61B 5/0205      (2006.01)
A61B 5/024       (2006.01)
A61B 5/145       (2006.01)
A61B 5/1455      (2006.01)
G06V 10/141      (2022.01)
G06V 40/16       (2022.01)
H04N 23/611      (2023.01)
H04N 23/65       (2023.01)
H04N 23/951      (2023.01)
H04N 25/46       (2023.01)
```

(52) U.S. Cl.
CPC ........ *H04N 23/951* (2023.01); *A61B 5/02416* (2013.01); *A61B 5/7221* (2013.01); *H04N 25/46* (2023.01)

(56) References Cited

U.S. PATENT DOCUMENTS

| | | |
|---|---|---|
| 9,042,615 B1 | 5/2015 | Bradley |
| 9,101,296 B2 | 8/2015 | Schroeder et al. |
| 9,489,817 B2 | 11/2016 | Gui |
| 9,600,069 B2 | 3/2017 | Publicover et al. |
| 9,696,859 B1 | 7/2017 | Heller |
| 9,766,699 B2 | 9/2017 | Skogo et al. |
| 9,866,754 B2 | 1/2018 | Eskilsson et al. |
| 10,152,869 B2 | 12/2018 | Peyrard |
| 10,231,614 B2 | 3/2019 | Krueger |
| 10,317,672 B2 | 6/2019 | Sarkar |
| 10,401,952 B2 | 9/2019 | Young |
| 10,466,779 B1* | 11/2019 | Liu .................. G02B 27/0093 |
| 10,650,533 B2 | 5/2020 | Mallinson |
| 10,757,328 B2 | 8/2020 | Thukral |
| 10,788,894 B2 | 9/2020 | Price |
| 10,795,435 B2 | 10/2020 | Fontanel |
| 2012/0069301 A1 | 3/2012 | Hirata |
| 2015/0199005 A1 | 7/2015 | Haddon |
| 2015/0335278 A1 | 11/2015 | Ashmore |
| 2016/0167672 A1 | 6/2016 | Krueger |
| 2016/0342835 A1 | 11/2016 | Kaehler |
| 2017/0000339 A1 | 1/2017 | Di Statsi |
| 2017/0219833 A1 | 8/2017 | Mayama |
| 2017/0227779 A1* | 8/2017 | Kato .................. H04N 5/64 |
| 2018/0068449 A1 | 3/2018 | Malaika et al. |
| 2018/0088340 A1 | 3/2018 | Amayeh et al. |
| 2018/0184002 A1 | 6/2018 | Thukral |
| 2018/0210547 A1 | 7/2018 | Sarkar |
| 2018/0284872 A1 | 10/2018 | Schluessler |
| 2018/0299953 A1 | 10/2018 | Selker et al. |
| 2019/0107823 A1* | 4/2019 | Hoferer .............. G05B 19/409 |
| 2019/0174039 A1 | 6/2019 | Jung et al. |
| 2019/0196179 A1 | 6/2019 | Sarkar et al. |
| 2019/0204912 A1 | 7/2019 | Yang et al. |
| 2019/0204913 A1 | 7/2019 | Sarkar et al. |
| 2019/0243472 A1* | 8/2019 | Stafford .............. G02B 27/017 |
| 2019/0350471 A1 | 11/2019 | Marks et al. |
| 2020/0026350 A1 | 1/2020 | Eash et al. |
| 2020/0041790 A1* | 2/2020 | Martinez .............. G02B 27/148 |
| 2020/0121184 A1 | 4/2020 | Hu |
| 2020/0278539 A1 | 9/2020 | Petljanski et al. |
| 2020/0285050 A1 | 9/2020 | Price et al. |
| 2020/0285307 A1 | 9/2020 | Price et al. |
| 2020/0285848 A1 | 9/2020 | Price et al. |
| 2020/0311978 A1 | 10/2020 | Aflaki Beni |
| 2020/0335032 A1 | 10/2020 | Kiik |
| 2020/0389582 A1 | 12/2020 | Herman |
| 2021/0049238 A1* | 2/2021 | Vaughn .................. G06N 20/00 |
| 2021/0169417 A1* | 6/2021 | Burton .................. A61B 5/4857 |
| 2023/0009372 A1 | 1/2023 | Macknik |

OTHER PUBLICATIONS

Akşit, Kaan, Jan Kautz, and David Luebke. "Gaze-sensing leds for head mounted displays." *arXiv preprint arXiv:2003.08499* (2020).

Angelopoulos, Anastasios N., et al. "Event based, near eye gaze tracking beyond 10,000 Hz." *arXiv preprint arXiv:2004.03577* (2020).

Ariz, Mikel, et al. "Optimizing the interoperability between a VOG and a EMG system." *COGAIN2009 Proceedings* (2009): 43.

Brunyé, Tad T., et al. "A review of eye tracking for understanding and improving diagnostic interpretation." *Cognitive research: principles and implications* 4.1 (2019): 1-16.

Chin, Craig A., et al. "Integrated electromyogram and eye-gaze tracking cursor control system for computer users with motor disabilities." (2008).

Choo, Kyojin D., et al. "5.2 energy-efficient low-noise CMOS image sensor with capacitor array-assisted charge-injection SAR ADC for motion-triggered low-power IoT applications." *2019 IEEE International Solid-State Circuits Conference—(ISSCC)*. IEEE, 2019.

Cognolato, Matteo, Manfredo Atzori, and Henning Müller. "Head-mounted eye gaze tracking devices: An overview of modern devices and recent advances." *Journal of rehabilitation and assistive technologies engineering* 5 (2018): 2055668318773991.

Cristina, Stefania, and Kenneth P. Camilleri. "Unobtrusive and pervasive video-based eye-gaze tracking." *Image and Vision Computing* 74 (2018): 21-40.

Dietz, Paul, William Yerazunis, and Darren Leigh. "Very low-cost sensing and communication using bidirectional LEDs." *International Conference on Ubiquitous Computing*. Springer, Berlin, Heidelberg, 2003.

Dutta, Anjan, et al. "Vision tracking: A survey of the state-of-the-art." *SN Computer Science* 1.1 (2020): 1-19.

Fuhl, Wolfgang, et al. "Pupil detection for head-mounted eye tracking in the wild: an evaluation of the state of the art." *Machine Vision and Applications* 27.8 (2016): 1275-1288.

Gilzenrat, Mark S., et al. "Pupil diameter tracks changes in control state predicted by the adaptive gain theory of locus coeruleus function." *Cognitive, Affective, & Behavioral Neuroscience* 10.2 (2010): 252-269.

Goni, Sonia, et al. "Robust algorithm for pupil-glint vector detection in a video-oculography eyetracking system." *Proceedings of the 17th International Conference on Pattern Recognition, 2004. ICPR 2004.* vol. 4. IEEE, 2004.

Griffith, Henry, Dmytro Katrychuk, and Oleg Komogortsev. "Assessment of shift-invariant CNN gaze mappings for PS-OG eye movement sensors." *Proceedings of the IEEE/CVF International Conference on Computer Vision Workshops.* 2019.

Horiuchi, Ryogo, Tomohito Ogasawara, and Norihisa Miki. "Fatigue assessment by blink detected with attachable optical sensors of dye-sensitized photovoltaic cells." *Micromachines* 9.6 (2018): 310.

Hosp, Benedikt, et al. "RemoteEye: An open-source high-speed remote eye tracker: Implementation insights of a pupil- and glint-detection algorithm for high-speed remote eye tracking." *Behavior research methods* 52.3 (2020).

Johns, Murray W., et al. "Monitoring eye and eyelid movements by infrared reflectance oculography to measure drowsiness in drivers." *Somnologie-Schlafforschung und Schlafmedizin* 11.4 (2007): 234-242.

Katrychuk, Dmytro, Henry K. Griffith, and Oleg V. Komogortsev. "Power-efficient and shift-robust eye-tracking sensor for portable VR headsets." *Proceedings of the 11th ACM Symposium on Eye Tracking Research & Applications.* 2019.

Katrychuk, Dmytro, Henry Griffith, and Oleg Komogortsev. "A Calibration Framework for Photosensor-based Eye-Tracking System." *ACM Symposium on Eye Tracking Research and Applications.* 2020.

(56) References Cited

OTHER PUBLICATIONS

Kolakowski, Susan M., and Jeff B. Pelz. "Compensating for eye tracker camera movement." *Proceedings of the 2006 symposium on Eye tracking research & applications.* 2006.

Li, Qiao, and Gari D. Clifford. "Dynamic time warping and machine learning for signal quality assessment of pulsatile signals." *Physiological measurement* 33.9 (2012): 1491.

Li, Richard, et al. "Optical gaze tracking with spatially-sparse single-pixel detectors." *2020 IEEE International Symposium on Mixed and Augmented Reality (ISMAR).* IEEE, 2020.

Li, Tianxing, and Xia Zhou. "Battery-free eye tracker on glasses." *Proceedings of the 24th Annual International Conference on Mobile Computing and Networking.* 2018.

Magdalena Nowara, Ewa, et al. "SparsePPG: Towards driver monitoring using camera-based vital signs estimation in near-infrared." *Proceedings of the IEEE conference on computer vision and pattern recognition workshops.* 2018.

Mantiuk, Radosław, et al. "Do-it-yourself eye tracker: Low-cost pupil-based eye tracker for computer graphics applications." *International Conference on Multimedia Modeling.* Springer, Berlin, Heidelberg, 2012.

Martins, R., and J. M. Carvalho. "Eye blinking as an indicator of fatigue and mental load—a systematic review." *Occupational safety and hygiene III* 10 (2015): 231-235.

Mastrangelo, Alexander S., et al. "A low-profile digital eye-tracking oculometer for smart eyeglasses." *2018 11th International Conference on Human System Interaction (HSI).* IEEE, 2018.

Messikommer, Nico, et al. "Event-based asynchronous sparse convolutional networks." *European Conference on Computer Vision.* Springer, Cham, 2020.

Mestre, Clara, Josselin Gautier, and Jaume Pujol. "Robust eye tracking based on multiple corneal reflections for clinical applications." *Journal of biomedical optics* 23.3 (2018): 035001.

Meyer, Johannes, et al. "A novel camera-free eye tracking sensor for augmented reality based on laser scanning." *IEEE Sensors Journal* 20.24 (2020): 15204-15212.

Padmanaban, Nitish, Robert Konrad, and Gordon Wetzstein. "Autofocals: Evaluating gaze-contingent eyeglasses for presbyopes." *Science advances* 5.6 (2019): eaav6187.

Pan, Liyuan, et al. "Bringing a blurry frame alive at high frame-rate with an event camera." *Proceedings of the IEEE/CVF Conference on Computer Vision and Pattern Recognition.* 2019.

Park, Seonwook, et al. "Few-shot Adaptive Gaze Estimation", IEEE/CVF International Conference on Computer Vision (ICCV), arXiv:1905.01941 (2019).

Rigas, Ioannis, Hayes Raffle, and Oleg V. Komogortsev. "Hybrid ps-v technique: A novel sensor fusion approach for fast mobile eye-tracking with sensor-shift aware correction." *IEEE Sensors Journal* 17.24 (2017): 8356-8366.

Rigas, Ioannis, Hayes Raffle, and Oleg V. Komogortsev. "Photosensor oculography: survey and parametric analysis of designs using model-based simulation." *IEEE Transactions on Human-Machine Systems* 48.6 (2018): 670-681.

Rostaminia, Soha, et al. "Ilid: low-power sensing of fatigue and drowsiness measures on a computational eyeglass." *Proceedings of the ACM on interactive, mobile, wearable and ubiquitous technologies* 1.2 (2017): 1-26.

Russo, J. Edward. "The limbus reflection method for measuring eye position." *Behavior Research Methods & Instrumentation* 7.2 (1975): 205-208.

Ryan, Cian, et al. "Real-time face & eye tracking and blink detection using event cameras." *Neural Networks* 141 (2021): 87-97.

Ryan, Wayne J., Andrew T. Duchowski, and Stan T. Birchfield. "Limbus/pupil switching for wearable eye tracking under variable lighting conditions." *Proceedings of the 2008 symposium on Eye tracking research & applications.* 2008.

Scheerlinck, Cedric, Nick Barnes, and Robert Mahony. "Asynchronous spatial image convolutions for event cameras." *IEEE Robotics and Automation Letters* 4.2 (2019): 816-822.

Schleicher, Robert, et al. "Blinks and saccades as indicators of fatigue in sleepiness warnings: looking tired?." *Ergonomics* 51.7 (2008): 982-1010.

Shi, Lixin, et al. "Light field reconstruction using sparsity in the continuous fourier domain." *ACM Transactions on Graphics (TOG)* 34.1 (2014): 1-13.

Sree, Niranjanaa Bose S. and Kandaswamy, A. "Sparse characterization of PPG based on K-SVD for beat-to-beat blood pressure prediction", Biomedical Research 29 (4), 835-843 (2018).

Swirski, Lech, Andreas Bulling, and Neil Dodgson. "Robust real-time pupil tracking in highly off-axis images." *Proceedings of the symposium on eye tracking research and applications.* 2012.

Tonsen, Marc, et al. "Invisibleeye: Mobile eye tracking using multiple low-resolution cameras and learning-based gaze estimation." *Proceedings of the ACM on Interactive, Mobile, Wearable and Ubiquitous Technologies* 1.3 (2017): 1-21.

Tonsen, Marc, Chris Kay Baumann, and Kai Dierkes. "A High-Level Description and Performance Evaluation of Pupil Invisible." *arXiv preprint arXiv:2009.00508* (2020).

Topal, Cihan, et al. "A low-computational approach on gaze estimation with eye touch system." *IEEE transactions on cybernetics* 44.2 (2013): 228-239.

Valliappan, Nachiappan, et al. "Accelerating eye movement research via accurate and affordable smartphone eye tracking." *Nature communications* 11.1 (2020): 1-12.

Vidal, Mélodie, et al. "Wearable eye tracking for mental health monitoring." *Computer Communications* 35.11 (2012): 1306-1311.

Wang, Joseph Tao-yi. "Pupil dilation and eye tracking." *A handbook of process tracing methods for decision research: A critical review and user's guide* (2011): 185-204.

Young, Laurence R., and David Sheena. "Survey of eye movement recording methods." *Behavior research methods & instrumentation* 7.5 (1975): 397-429.

Zemblys, Raimondas, et al. "Using machine learning to detect events in eye-tracking data." *Behavior research methods* 50.1 (2018): 160-181.

Zemblys, Raimondas, and Oleg Komogortsev. "Making stand-alone PS-OG technology tolerant to the equipment shifts." *Proceedings of the 7th Workshop on Pervasive Eye Tracking and Mobile Eye-Based Interaction.* 2018.

Zhao, Hongfan. "Micro-Scanning Mirror based Eye-tracking Technology." (2020).

International search report, PCT/IB2021/059791, date of mailing Jan. 27, 2022.

Written opinion of the international searching authority, PCT/IB2021/059791, date of mailing Jan. 27, 2022.

* cited by examiner

EFFICIENT IMAGE CAPTURING BASED ON EYELID POSITION

CROSS-REFERENCE TO RELATED APPLICATIONS

This Application is a Continuation of U.S. application Ser. No. 17/490,432, filed Sep. 30, 2021. U.S. application Ser. No. 17/490,432 claims priority to U.S. Provisional Patent Application No. 63/113,846, filed Nov. 14, 2020, U.S. Provisional Patent Application No. 63/122,961, filed Dec. 9, 2020, and U.S. Provisional Patent Application No. 63/140,453 filed Jan. 22, 2021

BACKGROUND

Eye tracking using video-oculography (VOG) is important for the performance of many head-mounted systems, such as mixed reality displays. For example, VOG can enable more efficient image rendering (through foveated rendering), as well as determining various pupil features that may be indicative of the user's physiological and emotional states. The performance of VOG, and the utility from information obtained using VOG, can be highly dependent on the quality of images of the eye that are captured, and in particular, on whether the user blinking at the time (which can lead to occlusion of the pupil in the captured images). The rate of typical eye blinking varies according to the person and the task performed, and is on average between of 4 and 17 blinks/minute, with an average duration of a blink being between 100 ms and 400 ms. Thus, during a significant amount of time, eye blinking can render images of the eye to be less useful for eye tracking.

Eye tracking using VOG can require expenditure of significant power by battery-operated head-mounted systems. But typical VOG systems do not take into account blinking when capturing images and/or processing captured images. Thus, there is a need to be able to account for blinking when performing eye tracking in order to save power with battery-operated systems.

SUMMARY

Eye blinking affects the performance of video-based eye trackers that cannot track the limbus and/or the pupil when occluded by the eyelid. In addition, when the eye is partially occluded by the eyelid, at the beginning and end of the blink, gaze point estimation accuracy may decrease.

Video cameras are not the only way to obtain data useful for eye tracking. Various types of head-mounted devices can provide measurements that are indicative of the eye's position and/or the eyelid's position. For example, optical flow sensors, range sensors, and photosensor-oculography devices (PSOG) can also provide information about the eye and/or eyelid's position. These types of devices are typically more power-efficient than VOG, but also typically provide less detailed and/or less accurate information about the eye and/or eyelid.

Some aspects of this disclosure involve eye tracking that utilizes information about the eyelid position in order to operate in a more efficient manner a head-mounted camera that is used for VOG. In some embodiments, a head-mounted device is utilized to detect eyelid position and then this information is used for timing the image capturing, and/or adjusting the size and/or region of the eye captured in the images, to include the visible portion of the eye. Because battery operated head-mounted systems usually strive to save power, and the head-mounted devices disclosed in embodiments described herein (e.g., PSOG, range sensors, etc.) may be more power efficient than VOG, using such head-mounted devices along with VOG, as described herein, can save power when performing eye tracking.

One aspect of this disclosure involves a system that operates a camera according to eyelid position. In one embodiment, the system includes an inward-facing head-mounted camera that captures images of an eye, a head-mounted device, and a computer. The head-mounted device emits electromagnetic waves towards the eye, and take measurements of reflections of the electromagnetic waves from the eye. Optionally, an average rate at which the measurements of the reflections are taken is at least ten times an average rate at which the images are captured. The computer detects, based on the measurements of the reflections, a position of at least one of the eyelids covering the eye (eyelid position). The computer operates the inward-facing head-mounted camera according to the eyelid position in a manner that decreases, in the captured images, areas depicting the at least one of the eyelids.

In one example, the head-mounted device comprises a photosensor-oculography device (PSOG) that measures reflections of light emitted by the PSOG towards the eye. In another example, the head-mounted device comprises an optical flow sensor that measures optical flow and/or visual motion, and the eyelid position is calculated based on an optical flow algorithm. In yet another example, the head-mounted device comprises range sensors that measure ranges between the range sensors and the eye (measurements of the range sensors are affected by the eyelid position).

In one embodiment, the inward-facing head-mounted camera utilizes a sensor that supports changing of its region of interest (ROI), and the computer utilizes the eyelid position to set the ROI around a portion of the eye that is not covered by the at least one of the eyelids. Optionally, the ROI covers less than half the sensor's field of view. Optionally, the computer sets the ROI such that the size of the ROI is proportional to area of the eyeball uncovered by the eyelid. Optionally, the computer detects a raising of the upper eyelid based on the measurements of the reflections, and increases a frame rate of the inward-facing head-mounted camera during the time the upper eyelid is raised above a threshold. Optionally, the computer detects a raising of the lower eyelid based on the measurements of the reflections, and increases a frame rate of the inward-facing head-mounted camera during the time the lower eyelid is raised above a threshold.

In one embodiment, in order to operate the inward-facing head-mounted camera according to the eyelid position the computer refrains from commanding the camera to capture the images during blinks and/or while the eye is closed.

In one embodiment, the computer extracts eyelid positions by analyzing the images (image-based positions), and utilizes the image-based positions and the measurements of the reflections to generate labeled training samples for training a machine learning-based model for detecting the eyelid position based on additional measurements of reflections taken with the head-mounted device.

In another embodiment, the computer receives photos from a camera belonging to a non-head-mounted device, extracts eyelid positions by analyzing the photos (photo-based positions), and utilizes the photo-based positions and the measurements of the reflections to generate labeled training samples for training a machine learning-based model for detecting the eyelid position based on additional measurements of reflections taken with the head-mounted device. Optionally, the computer comprises a head-mounted computer and a non-head-mounted computer that communicate over a wireless communication channel, the non-head-mounted computer trains the model, and the head-mounted computer uses the trained model for detecting the eyelid position based on reflections.

Another aspect of this disclosure involves a method that includes at least the following steps: capturing images of an eye by an inward-facing head-mounted camera; emitting, by a head-mounted device, electromagnetic waves towards the eye, and taking measurements of reflections of the electromagnetic waves from the eye, where an average rate of taking measurements of the reflections is at least ten times an average rate of capturing the images; detecting, based on the measurements of the reflections, a position of at least one of the eyelids covering the eye (eyelid position); and operating the inward-facing head-mounted camera according to the eyelid position in a manner that decreases, in the captured images, areas depicting the at least one of the eyelids.

In one embodiment, the inward-facing head-mounted camera utilizes a sensor that supports changing of its region of interest (ROI), and the method includes a step of utilizing the eyelid position to set the ROI around a portion of the eye that is not covered by the at least one of the eyelids.

In one embodiment, the method optionally involves performing the following steps to train a machine learning-based model that is used for detecting the eyelid position based on additional measurements of reflections: extracting eyelid positions by analyzing the images (image-based positions); generating labels based on the image-based positions; generating feature values based on the measurements of the reflections; and providing the labels and feature values to train the machine learning-based model for detecting the eyelid position based on the additional measurements of the reflections.

In one embodiment, the method optionally involves performing the following steps to train a machine learning-based model that is used for detecting the eyelid position based on additional measurements of reflections: receiving photos from a camera belonging to a non-head-mounted device, extracting eyelid positions by analyzing the photos (photo-based positions), generating labels based on the photo-based positions, generating feature values based on the measurements of the reflections, and providing the labels and feature values to train the machine learning-based model for detecting the eyelid position based on the additional measurements of the reflections.

Yet another aspect of this disclosure involves a non-transitory computer readable medium storing one or more computer programs configured to cause a processor-based system to execute steps of one or more embodiments of the aforementioned method.

BRIEF DESCRIPTION OF THE DRAWINGS

The embodiments are herein described by way of example only, with reference to the following drawings.

DETAILED DESCRIPTION

Figure 1:
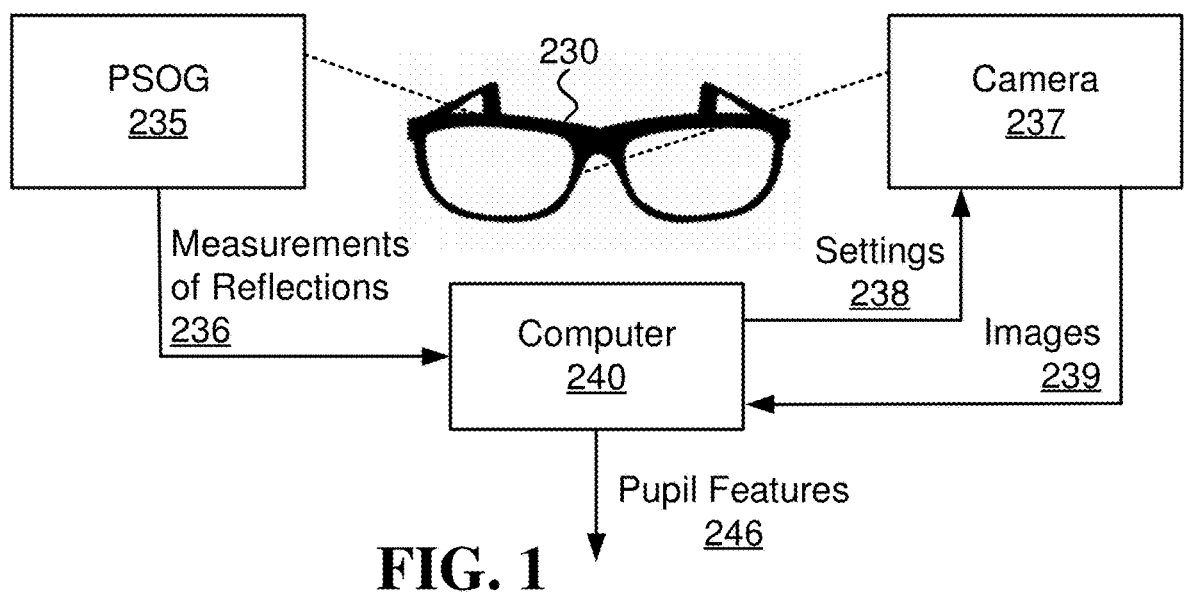
FIG. 1 illustrates an embodiment of an eye tracking system that includes a photosensor-oculography device (PSOG) and a camera.

The term "oculography" as used herein refers to measuring eye position and/or eye movements of either one eye or both eyes (i.e., monocular or binocular measurements). When supported by the system, oculography may also measure other eye parameters, such as pupil diameter and/or extent of blinking.

The term "eye tracking" as used herein refers to measuring eye position, eye movement, and/or gaze direction. An "eye tracker" is a device that measures and/or calculates values indicative of eye position, eye movement, and/or gaze direction. Some embodiments of an "eye tracking system" described herein may be considered an eye tracker, a component of an eye tracker, or a component that provides data utilized by an eye tracker. When supported, an eye tracking system may measure other eye parameters, such as pupil diameter and/or extent of blinking.

As used herein, the terms "photosensor-oculography" and "photosensor-oculography device" (referred to herein as "PSOG"), refer to measuring eye position and/or eye movements (or equivalents thereof) and/or of a device used for said measuring, based on the context. Measurements of the eye position and/or the eye movements, may be measurements of either of one eye or both eyes (depending on the context) Taking such measurements is done based on the principle of emitting light and capturing the reflected light from the user's eye surface and/or eyelid with discrete photosensors. Alternative terms known in the art for PSOG include PS-OG, photoelectric-technique, infrared-oculography, infrared-reflectance-oculography, limbus-reflection-technique, and eye tracking based on steering a beam through MEMS. The following reference, which is referred to herein as Rigas 2018, and which is incorporated herein by reference, provides a review of PSOG techniques: Rigas, Ioannis, Hayes Raffle, and Oleg V. Komogortsev "Photosensor oculography: Survey and parametric analysis of designs using model-based simulation" IEEE Transactions on Human-Machine Systems 99 (2018): 1-12.

The term "discrete photosensors" refers to very-low resolution light detectors that are relatively low cost and low power, such as photosensitive sensors, photodetectors, photodiodes, Light Emitting Diodes (LEDs) having a bi-directional characteristic with the ability to emit the light and to measure reflections, single detectors, split detectors, four-quadrant detectors, position-sensitive detectors, photo reflective sensors (for modules combining both the emitter and receiver), sensors with less than a thousand sensing pixels on the same substrate (i.e., the term discrete photosensor is not limited to a single-pixel photosensor), and arrays with direct wire connections to each pixel supporting parallel readout. The definition of discrete photosensors explicitly excludes camera sensors having thousands/millions of pixels that are equipped with suitable optics for so many pixels, such as CCD and CMOS video camera sensors having thousands/millions of pixels.

PSOG, as defined herein, may also be implemented using a scanning light beam. For example, U.S. Pat. No. 10,317,672 and U.S. patent applications 2018/0210547, 2019/0204912, and 2019/0204913 to AdHawk Microsystems describe a version of PSOG that is based on steering a light beam using a microelectromechanical system (MEMS) onto a surface of the eye, and detecting light reflected from features of the eye with one or more photosensors. In another example, US patent application 2020/0285307 to Microsoft Technology Licensing LLC describes another version of PSOG that is based on steering a light beam using MEMS and through a display module assembly onto the eye, and detecting the reflections with one or more photodetectors. In still another example, the thesis of Zhao, Hongfan "Micro-Scanning Mirror based Eye-tracking Technology" (2020), describes still another version of PSOG that is based on a scanning-micro-minor to scan a laser beam on the eyeball, and a linear array photodetector to detect the light reflected from the eyeball.

Sentences in the form of "to calculate Y based on the reflections measured by the PSOG" or "to calculate Y based on measurements of reflections (taken by the PSOG)" are to be interpreted in the context of the structure and operation of the PSOG. For example, when the PSOG includes multiple light sources and multiple discrete photosensors, the reflections are indicative of which light source is emitting at a given time and intensities of the corresponding measured reflections due to those emissions. In a second example, the PSOG includes a scanning light beam and multiple discrete photosensors, and the reflections are indicative of the directions of the scanning light beam and the corresponding reflections measured by the photosensors. In a third example, the reflections are indicative of one or more of the following eye parameters calculated by the PSOG: eye position, eye movement, eye movement velocity, upper and/or lower eyelid position, and blinking.

Measurements of the reflections may be expressed using various units, in different embodiments. In some embodiments, the measurements of the reflections may be the raw output of the photosensors expressed as values of voltage or illuminance (e.g., expressed as lux). In some embodiments, the measurements of the reflections may undergo various preprocessing and/or filtering using techniques known in the art.

The term "video-oculography" (VOG), as used herein, refers to measuring eye position and/or eye movements (or equivalents thereof), of either one eye or both eyes, based on processing of images captured by one or more video cameras. Alternative terms known in the art for video-oculography include "video-based eye-tracker", "video-based eye-gaze tracking", "Infrared OcculoGraphy", "video-nystagmography", and "infrared video in electronystagmography". The following references, which are incorporated herein by reference, provide reviews of video-oculography techniques and their usages: (i) Tonsen, Marc, Chris Kay Baumann, and Kai Dierkes "A High-Level Description and Performance Evaluation of Pupil Invisible" arXiv preprint arXiv:2009.00508 (2020), (ii) Cristina, Stefania, and Kenneth P. Camilleri "Unobtrusive and pervasive video-based eye-gaze tracking" Image and Vision Computing 74 (2018): 21-40, and (iii) Brunyé, Tad T., et al. "A review of eye tracking for understanding and improving diagnostic interpretation" Cognitive research: principles and implications 4.1 (2019): 1-16.

In some embodiments, a camera used for VOG captures intensities, such as the cameras used by the above VOG references, and the images captured by the camera represent the intensities measured by the pixels.

In other embodiments, a camera used for VOG may be an event camera (also known as a neuromorphic camera, silicon retina, or dynamic vision sensor) that outputs data that comprises pixel-level brightness changes. In these embodiments, the pixels of the event camera may operate independently and asynchronously, and report changes in brightness as they occur.

When a camera used in VOG is an event camera, the word "images" in sentences like "a camera configured to capture images (of the eye)" refers to data captured by the camera, which may be images (e.g., frames) and/or data that may be converted to images and/or equivalents thereof for the purpose of additional computations (e.g., by serving as input for machine learning-based methods). In one embodiment, the images are reconstructed based on events reported by the event camera, such as the approach disclosed by U.S. Pat. No. 10,466,779 that is incorporated herein by reference. In another embodiment, events captured by an event camera may be converted into synchronous dense, image-like representations, which can be processed by traditional machine learning methods developed for standard cameras. Such an approach is disclosed by Messikommer, Nico, et al. "Event-based Asynchronous Sparse Convolutional Networks" arXiv preprint arXiv:2003.09148 (2020). In yet another embodiment, an event camera may capture both frames and events. Thus, a reference to "images" in such cases may refer both frames of intensities (e.g., acquired through synchronous reading of photodiodes) and asynchronous events. This type of images is disclosed by U.S. Pat. No. 10,466,779 and by the reference Angelopoulos, Anastasios N., et al. "Event Based, Near Eye Gaze Tracking Beyond 10,000 Hz" arXiv preprint arXiv:2004.03577 (2020), which are incorporated herein by reference.

Various embodiments described herein involve a head-mounted system (HMS) that includes VOG and/or PSOG. In these embodiments, the VOG and/or PSOG include one or more light emitting components and/or one or more sensing components that may be part of the HMS.

Some examples of the one or more emitting components that may be utilized by systems that include VOG and/or PSOG (such as the aforementioned HMS) include various types of LED or laser emitters. Optionally, these devices are coupled to a head-mounted system at various positions suitable to emit light to the wearer's eyes. In one example, emitters may be embedded in a head-mounted frame. In another example, emitters may be embedded in the smartglasses' temples. In yet another example, emitters may be embedded in a display (e.g., a microLED display with IR emitters located in front of an eye, such as disclosed in U.S. patent application 2020/0335032). In still another example, emitters may be configured to direct their light to the eye through a waveguide (e.g., emitters coupled to an augmented reality display module waveguide located in front of the eyes, such as disclosed in U.S. patent application 2020/0285307).

Some examples of the one or more sensing components that may be utilized by systems that include VOG and/or PSOG (such as the aforementioned HMS) include various types of photosensors (e.g., discrete photosensors or imaging sensors of cameras). In one example, photosensors may be embedded in a head-mounted frame. In another example, photosensors may be embedded in smartglasses' temples. In yet another example, photosensors may be embedded in a display located in front of an eye). In still another example, photosensors may be configured to receive the reflected light from a waveguide (e.g., photosensors coupled to an augmented reality display module waveguide located in front of the eyes).

In various embodiments disclosed herein VOG may be used in conjunction with PSOG. For example, an HMS may include one or more components that enable VOG and also one or more additional components that enable PSOG. There may be various reasons and motivations for having PSOG along with VOG in some embodiments of eye tracking systems, such as saving power, improving accuracy of eye tracking, and/or extending the range of trackable eye positions, as discussed below.

Due to the different nature of the signals being analyzed, VOG is typically more accurate than PSOG when it comes to the task of eye tracking (e.g., VOG will often make more accurate determinations of eye positions than PSOG). However, when tracking the eye positions at the same rate, PSOG typically consumes significantly less power than VOG, and thus PSOG is considered low-power relative of VOG. The reference Rigas, Ioannis, Hayes Raffle, and Oleg V. Komogortsev "Hybrid ps-v technique: A novel sensor fusion approach for fast mobile eye-tracking with sensor-shift aware correction" IEEE Sensors Journal 17.24 (2017): 8356-8366, (referred to herein as Rigas 2017, and is incorporated herein by reference), discloses a system combining VOG and PSOG, which is able to calibrate sensor shifts affecting the PSOG models based on the accurate results of the VOG.

Although the hybrid eye tracker of Rigas 2017 reduced the power consumption significantly, the reduction is not sufficient for a lightweight HMS, and as a result both the authors of Rigas 2017, and all the other authors of the publications citing Rigas 2017, directed their efforts towards developing a standalone PSOG (without VOG) that is robust to sensor shifts. Three examples of the current research directions following Rigas 2017 include (i) Zemblys, Raimondas, and Oleg Komogortsev "Making stand-alone PS-OG technology tolerant to the equipment shifts" Proceedings of the 7th Workshop on Pervasive Eye Tracking and Mobile Eye-Based Interaction, 2018, (ii) Katrychuk, Dmytro, Henry K. Griffith, and Oleg V. Komogortsev "Power-efficient and shift-robust eye-tracking sensor for portable VR headsets" Proceedings of the 11th ACM Symposium on Eye Tracking Research & Applications, 2019, and (iii) Li, Richard, et al. "Optical Gaze Tracking with Spatially-Sparse Single-Pixel Detectors" arXiv preprint arXiv:2009.06875 (2020). However, the inventors of this invention do not overwhelmingly agree with the current trend of aspiring to a standalone PSOG (which is also taken by the above cited references discussing PSOG with MEMS scanning beam). The inventors believe it is better to further optimize the power consumption and/or the hardware architecture and operation of the combined VOG and PSOG system, as described below.

Some of the embodiments disclosed herein may combine VOG and PSOG. This combination may be done in various ways. In some embodiments, PSOG may be operated essentially independently from the VOG. Optionally, in these embodiments, the high-rate, low-power PSOG measurements may be used to optimize the performance of the lower-rate, higher-power VOG. In other embodiments, the more accurate VOG may be used to correct errors in eye parameters derived from PSOG, while optimizing the operation of the VOG based on the PSOG measurements, in order to improve the performances of known methods (such as described in Rigas 2017) to make them suitable for a wireless HMS.

In one embodiment, a sensor fusion algorithm is utilized to combine VOG and PSOG measurements. This algorithm includes the following steps:

In step 1, the computer receives images from the head-mounted camera, and determines the eye position based on at least one of the images. The computer may also determine gaze based on images of both eyes. The gaze may be relative to the frame used to mount the cameras, relative to the user's head, and/or relative to other suitable coordinates known in the art.

In step 2, the computer calculates one or more values related to the eye based on measurements of reflections taken by the PSOG. In one example, the measurements of the reflections include identification of the light source emitting the light and intensities of the corresponding measured reflections measured by the PSOG. In this step, the computer calculates one or more values related to the eye, such as eye position, eye movement, and/or eye movement velocity. Usually, the PSOG measurements have lower latency and lower accuracy compared to the VOG measurements.

And in step 3, the computer combines the VOG and PSOG measurements for at least one of (i) calibrating the PSOG models based on the VOG results, and (ii) improving the accuracy of the higher-frequency lower-accuracy PSOG results based on the lower-frequency higher-accuracy VOG results. Examples of known algorithms, useful for sensor fusion that combines the VOG and PSOG measurements, include Kalman filter, Bayesian network, and convolutional neural network. The combined measurements may also be used to predict future values related to the eye, such as a future eye position or a future gaze direction. In some examples, these future values are used for foveated rendering, for setting the camera's windowing parameters, for setting the camera's timings of capturing images, and/or for setting the camera's smart binning parameters.

Various embodiments described herein involve calculations based on machine learning approaches. Herein, the terms "machine learning approach" and/or "machine learning-based approaches" refer to learning from examples using one or more approaches. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems. Herein, a "machine learning-based model" is a model trained using one or more machine learning approaches.

Herein, "feature values" (also known as feature vector, feature data, numerical features, and inputs) may be considered input to a computer that utilizes a model to perform the calculation of a value (e.g., an output, "target value", or label) based on the input. It is to be noted that the terms "feature" and "feature value" may be used interchangeably when the context of their use is clear. However, a "feature" typically refers to a certain type of value, and represents a property, while "feature value" is the value of the property with a certain instance (i.e., the value of the feature in a certain sample).

In addition to feature values generated based on measurements taken by sensors mentioned in a specific embodiment, at least some feature values utilized by a computer of the specific embodiment may be generated based on additional sources of data that were not specifically mentioned in the specific embodiment. Some examples of such additional sources of data include: contextual information, information about the user being, measurements of the environment, and values of physiological signals of the user obtained by other sensors.

Sentences in the form of "inward-facing head-mounted camera" refer to a camera configured to be worn on a user's head and to remain pointed at the region it captures (sometimes referred to as ROI), which is on the user's face, also when the user's head makes angular and lateral movements. A head-mounted camera (which may be inward-facing and/or outward-facing) may be physically coupled to a frame worn on the user's head, may be physically coupled to eyeglasses using a clip-on mechanism (configured to be attached to and detached from the eyeglasses), may be physically coupled to a hat or a helmet, or may be mounted to the user's head using any other known device that keeps the camera in a fixed position relative to the user's head.

The term "smartglasses" refers to any type of a device that resembles eyeglasses, which includes a frame configured to be worn on a user's head and electronics to operate one or more sensors.

The term "visible-light camera" refers to a non-contact device designed to detect at least some of the visible spectrum, such as a video camera with optical lenses and CMOS or CCD sensor; visible-light camera may be sensitive to near-infrared wavelengths below 1050 nanometer. The term "thermal camera" refers to a non-contact device that measures electromagnetic radiation having wavelengths longer than 2500 nanometer (nm) and does not touch the region it measures. A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

A reference to a "camera" herein may relate to various types of devices. In one example, a camera may be a visible-light camera. In another example, a camera may capture light in the ultra-violet range. In another example, a camera may capture near-infrared radiation (e.g., wavelengths between 750 and 2000 nm). And in still another example, a camera may be a thermal camera.

The term "temperature sensor" refers to a device that measures temperature and/or temperature change. The temperature sensor may be a contact thermometer (such as a thermistor, a thermocouple), and/or a non-contact thermal cameras (such as a thermopile sensor, a microbolometer sensor, or a cooled infrared sensor). Some examples of temperature sensors useful to measure skin temperature include: thermistors, thermocouples, thermoelectic effect, thermopiles, microbolometers, and pyroelectric sensors. Some examples of temperature sensors useful to measure environment temperature include: thermistors, resistance temperature detectors, thermocouples; thermopiles, and semiconductor-based sensors.

The term "movement sensor" refers to a sensor comprising one or more of the following components: a 3-axis gyroscope, a 3-axis accelerometer, and a magnetometer. The movement sensor may also include a sensor that measures barometric pressure.

The term "acoustic sensor" refers to a device that converts sound waves into an electrical signal. The acoustic sensor may be a microphone, such as a dynamic microphone, a piezoelectric microphone, a fiber-optic microphone, a Micro-Electrical-Mechanical System (MEMS) microphone, and/or other known sensors that measure sound waves.

FIG. 1 illustrates an embodiment of an eye tracking system. Embodiments of this system include a PSOG 235 that emits light and measures reflections of the light from an eye of a user, a camera 237 that captures images 239 of the eye of the user, and a computer 240 that utilizes measurements 236 of the reflections and the images 239 to perform operations involved in tracking the eye of the user. It is noted that a phrase such as "images of the eye" is to be interpreted as images of at least portions of the eye and/or the eyelid.

In some embodiments, the PSOG 235 and the camera 237 are both coupled to a frame of smartglasses 230. In FIG. 1, as well as illustrations of other systems in this disclosure that include devices (e.g., PSOG, cameras, etc.) that are coupled to frames of smartglasses, a dotted line connecting a component to the frames, such as the lines in FIG. 1 between the PSOG 235 and the smartglasses 230 or the line between the camera 237 the smartglasses 230, are meant to indicate that the components are coupled to frames. This line is for illustration purposes only, and is meant to illustrate the fact that the components are coupled to the frames. The line is not meant to indicate a specific location on the frames at which the components are to be coupled and/or a nature of the coupling.

It is to be noted that embodiments described herein that include PSOG and/or cameras that are utilized for eye tracking may include multiple PSOG and cameras. For example, the smartglasses 230 may include one or more PSOGs, in addition to the PSOG 235, which may be utilized to track the same eye of the user that is tracked utilizing the PSOG 235, or to track the user's other eye. Additionally, implementations PSOG used in embodiments described herein (such as the PSOG 235) may involve utilization of various combinations of emitters and photosensor detectors. Some examples of combinations of different numbers/locations of emitters and/or photosensor detectors are discussed in references mentioned herein (e.g., Rigas 2018).

In one embodiment, the computer 240 is configured to calculate values indicative of eye movement velocity (EMV) based on the measurements 236 of the reflections, and utilize the values to determine settings 238 that control how data is read from the camera 237. Optionally, the computer 240 reads data from the camera 237 at a higher bitrate when the values are indicative of the EMV being below a threshold compared to a lower bitrate at which data is read from the camera 237 when the values are indicative of the EMV being above the threshold. Additionally or alternatively, the computer 240 may calculate pupil features 246, based on the images 239, at a higher rate when the values are indicative of the EMV being below a threshold compared to when the values are indicative of the EMV being above the threshold.

EMV can be calculated by the computer 240 based on the change to eye positions over time. For example, at a certain time, the velocity may be calculated based on differences between two or more measurements of eye positions, conducted over a short period (such as successive eye position calculations performed based on the measurements 236 of the reflections). To calculate the eye positions and/or eye movements, the computer 240 may utilize various techniques known in the art, such as the techniques described in Rigas 2017 and/or other references involving PSOG, which are mentioned herein. Eye positions and eye velocities are typically described in terms of angular movement. Thus, the EMV can be expressed in some embodiments in term of angular velocity (i.e., degrees/second). Alternatively, in some embodiments, EMV may be expressed in absolute distances in which the eye moves. For example, in these embodiments, the EMV and the threshold may be expressed in units of centimeters/second.

In one example, the threshold may correspond to an EMV of 40°/second. In another example, the threshold may correspond to an EMV of 30°/second. In yet another example, the threshold may correspond to an EMV of 100°/second. In still other examples, the threshold may have a value that corresponds to an EMV that is a certain value that falls within the range of 20°/second to 150°/second. Herein, "bitrate" refers to the volume of data (e.g., expressed in bits or bytes) that is read in a given period of time. For example, a bitrate as used herein may be expressed in terms of bytes/second.

In some examples, the values indicative of EMV, which are calculated based on the measurements 236 of the reflections, may include values of angular velocity of the eye (e.g., expressed as a degrees/second of eye movement). In other examples, the values indicative of EMV, may include values amplitudes of eye movements expressing the angular distance an eye traveled during a certain window of time.

In some embodiments, the rate at which the values indicative of EMV are calculated is higher than the rate at which the images 239 are captured. For example, the images 239 may be captured at a rate that is below 100 Hz (e.g., 50 or 60 Hz), while the values are calculated at a rate that is significantly higher, such as 500 Hz, 1000 Hz, or more.

Reading data from the camera 237 at a higher bitrate, such as when the values are indicative of the EMV being below the threshold, compared to a lower bitrate, such as the bitrate at which data is read from the camera 237 when the values are indicative of the EMV being above the threshold, may be done in different ways in different embodiments.

In one embodiment, the computer 240 does not read image data from the camera 237 when the values calculated based on the measurements 236 of the reflections are indicative of the EMV being above the threshold. Optionally, the bitrate at which data is read from the camera 237 when the values are indicative of the EMV being above the threshold is less than 10% of the bitrate at which data is read from the camera 237 when the values are indicative of the EMV being below the threshold. Optionally, the bitrate at which data is read from the camera 237 when the values are indicative of the EMV being above the threshold is zero.

In another embodiment, the computer 240 reads image data at a higher frequency when the values calculated based on the measurements 236 of the reflections are indicative of the EMV being below the threshold compared to when said values are indicative of the EMV being above the threshold. Optionally, the resolution of the images read from the camera 237 at these different times is the same. In one example, the computer 240 reads first images, from among the images 239, at a frequency that is at least 50 Hz when the values are indicative of the EMV being below the threshold, and the computer 240 reads second images, from among the images 239, at a frequency that is below 50 Hz when the values are indicative of the EMV being above the threshold. In another example, the computer 240 reads images, from among the images 239, at a frequency that is below 10 Hz when the values are indicative of the EMV being above the threshold.

In yet another embodiment, the computer 240 reads images with a higher resolution when the values calculated bases on the measurements 236 of the reflections are indicative of the EMV being below the threshold compared to when said values are indicative of the EMV being above the threshold. Optionally, the frequency at images read from the camera 237 at these different times is the same.

Calculations of the values indicative of the EMV may be done at various rates in different embodiments. In some embodiments, calculations of these values are performed at a frequency at which measurements 236 of the reflections are taken by the PSOG 235, such as 500 Hz, 1000 Hz or more. In other embodiments, the values indicative of the EMV may be calculated at a lower frequency than the frequency at which the measurements 236 of the reflections are taken. For example, the values may be calculated at frequency of 100 Hz or lower. Thus, decisions made based on values indicative of the EMV, such as a rate at which to read data from the camera 237 and/or a rate at which to calculate the pupil features 246 may be done at various frequencies. For example, the settings 238 of the camera may be updated at different rates or asynchronously (e.g., as the indication of whether the EMV is above or below the threshold change).

Different eye tracking parameters may bring different values in different scenarios/experiments. These differences can help the system to save power by using the EMV to set the computer 240 to read the data from the camera 237 at different bitrates during eye fixation, smooth pursuits, and saccades. For example, when a researcher is interested in spatial attention, eye tracking data during a smooth pursuit may be more valuable than eye tracking data during fixation, and thus the system can save power by reading the data from the camera at a higher bitrate during smooth pursuits versus the bitrate at which data is read during eye fixations. And when the researcher is more interested in generating a heat map representing visual attention, then eye tracking data obtained during a fixation may be more valuable than eye tracking data obtained during a smooth pursuit, and the system may read the data from the camera 237 at a higher bitrate during fixations versus the bitrate at which data is read during smooth pursuits.

The computer 240 may utilize, in some embodiments, the values indicative of the EMV, to detect eye fixations, smooth pursuit eye movements, and/or saccades, and to read the data from the camera 237 at different bitrates during the eye fixations, the smooth pursuit, and the saccades. Optionally, average bitrates at which the data is read from the camera 237 during the eye fixations and the smooth pursuit eye movements are at least three times greater than an average bitrate at which the data is read from the camera 237 during saccades.

In one embodiment, the computer 240 is configured to set timing of the camera 237 to capture above 80% of the images 239 when the values calculated based on measurements 236 of the reflections are indicative of the EMV being below the threshold. In one example, having the EMV be above the threshold is indicative of saccades, and on average, images captured when there are no saccades are sharper than images captured during saccades.

When used for eye tracking, a PSOG-based system will typically consume significantly less power than a VOG-based system, if eye parameters are calculated by both systems at the same rate. Therefore, a combination of both PSOG and VOG can enable utilization of the typically more accurate (but power hungry) VOG at times that are likely to yield more useful and/or accurate eye parameters. Thus, identifying when the EMV is below the threshold (using the PSOG), can be used to trigger the use of VOG to calculate eye parameters during eye fixations, while avoiding the use of VOG during times of saccades that are likely to yield less accurate or useful eye parameters.

In one example, the PSOG 235 consumes below 1 mW while VOG (using the camera 237) consumes above 100 mW for eye tracking at the same rate. Because the higher the bitrate read from the camera 237 the more power is consumed for eye tracking that is based (at least in part) on images taken by the camera 237, using the PSOG 235 to trigger reading the camera 237 when the values are indicative of the EMV being below the threshold should reduce the power consumption of the system. Examples of values for the threshold may be around 40°/second (i.e., angular speed of the eye of 40° per second), to cover normal smooth pursuits the threshold may be up to 30°/second, and the threshold may be around 100°/second to cover fast smooth pursuits combined with catch-up saccades.

PSOG, as the term is used herein, may involve utilization of one or more light sources and/or one or more detectors, such as discrete photosensors, that detect reflections of the light emitted from the one or more light sources (and possibly external light sources too).

Figure 2A:
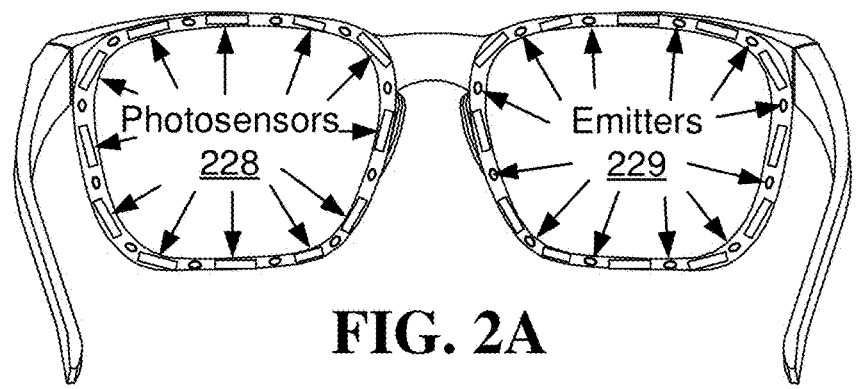
FIG. 2A illustrates smartglasses with PSOG that utilizes multiple light sources and multiple detectors.

FIG. 2A illustrates smartglasses with PSOG that utilizes multiple light sources and multiple detectors. Coupled to the frame of the smartglasses, around each of the lenses, are multiple photosensors 228 and multiple light sources (emitters 229), which are interleaved between the photosensors 228. It is to be noted that the emitters and photosensors are present on the frame around both lenses, but for the sake of clarity the photosensors 228 are designated on the left side and the emitters 229 are designated on the right side.

In one embodiment, the PSOG 235 includes: at least two light sources configured to emit the light, and at least three discrete photosensors configured to measure the reflections. Optionally, the discrete photosensors are spread over more than 2 cm.

In another embodiment, the PSOG 235 comprises at least two Light Emitting Diodes (LEDs) having a bi-directional characteristic with the ability to emit the light and to measure the reflections. Optionally, each of the at least two LEDs is sensitive to wavelengths equal to or shorter than the predominant wavelength it emits. Optionally, each of the at least two LEDs provides illumination when a forward voltage is applied to its electrical terminals, and acts as photodetector/photodiode for example by the following three steps: (i) apply a reverse voltage pulse for a short duration, (ii) discharge the LED's capacitance immediately afterwards, and (iii) measure the voltage across the LED to determine how much discharge of capacitance took place after a certain time. This technique is well known in the art and is further explained in publications such as (A) Akşit, Kaan, Jan Kautz, and David Luebke "Gaze-Sensing LEDs for Head Mounted Displays" arXiv preprint arXiv: 2003.08499 (2020), and (B) Dietz, Paul, William Yerazunis, and Darren Leigh "Very low-cost sensing and communication using bidirectional LEDs" International Conference on Ubiquitous Computing, Springer, Berlin, Heidelberg, 2003.

In some embodiments, the camera 237 utilizes a sensor that has more than 100 pixels. In these embodiments, the camera 237 may also have a lens, and the sensor plane of the camera 237 may be tilted by more than 2° relative to the lens plane of the camera 237, according to the Scheimpflug principle in order to capture sharper images.

Figure 2B:
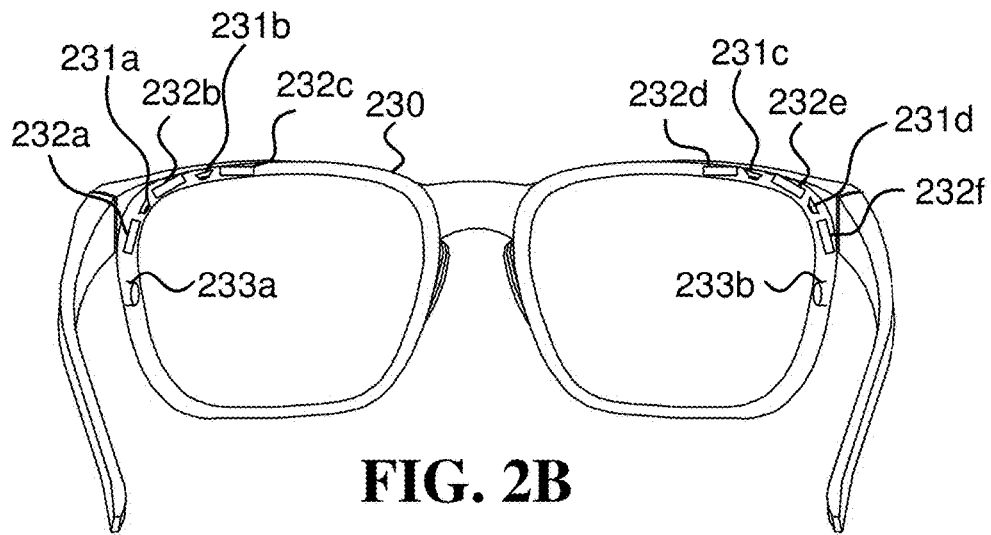
FIG. 2B illustrates an embodiment of an eye tracking system on smartglasses that tracks both eyes.

FIG. 2B illustrates an embodiment of an eye tracking system on smartglasses that tracks both eyes, which utilizes multiple light sources and detectors to track each eye. The illustrated system includes the smartglasses 230 that have PSOG and VOG that may be used together to track movements of both eyes. Tracking of the left eye is done utilizing a PSOG that includes multiple light sources (emitters 231a and 231b in the figure) as well as multiple detectors (discrete photosensors 232a, 232b, and 232c). Additionally, video camera 233a may be utilized to capture images of the left eye, which can be used to determine positions and/or movements of the left eye. In a similar fashion, tracking the right eye is done in this embodiment utilizing another PSOG that includes additional light sources (emitters 231c and 231d in the figure) as well as additional multiple detectors (discrete photosensors 232d, 232e, and 232f) and an additional video camera 233b that may be utilized to capture images of the right eye.

Knowing positions and/or movements of both eyes can be utilized to estimate the gaze of the user. In one embodiment, the eye tracking system includes an another PSOG (e.g., as illustrated in FIG. 2B) In this embodiment, the computer 240 calculates a gaze direction based on the measurements 236 of the reflections, measured by the PSOG 235, and additional measurements of reflections (of the other eye) taken by the other PS OG. For example, the computer 240 may utilize techniques known in the art to determine the user's gaze direction based on the eye positions of each of the eyes as determined based on measurements of the PSOG 235 and the additional measurements of reflections taken by the other PSOG. For example, the gaze may be determined using one or more of the computational techniques discussed in the references mentioned above that disclose a standalone PSOG.

Light sources may be utilized in different ways in order to conserve power and/or improve quality of images taken by the eye tracking system. In one embodiment, the computer 240 is configured to command the PSOG 235 to emit light with a higher intensity while the images 239 are being taken, compared to the average intensity of light emitted by the PSOG 235 while measuring reflections at times at which the images 239 are not being taken. Added illumination by emitters of the PSOG 235 may assist in making the images 239 clearer, compared to images taken while the emitters of PSOG 235 do not operate. In another embodiment, in which the PSOG 235 comprises multiple light sources that emit the light, while most of the measurements 236 of the reflections are taken, the PSOG 235 emits light from a single light source at a time. In this embodiment, for most of the images 239 that are captured, the PSOG 235 emits light from multiple light sources during the exposure time of the camera 237 (in which the images 239 are captured).

Utilizing the PSOG 235 to determine when and/or to what extent to utilize the camera 237 for eye tracking can be useful when the camera 237 is battery-operated, such as when it is embedded in a wearable device (e.g., smartglasses) or a mobile device (e.g., a smartphone).

In one embodiment, the camera 237 and the computer 240 are head-mounted and the PSOG 235 is more power-efficient than the camera 237 (meaning that if the PSOG 235 and the camera 237 operate taking their respective measurements for the same amount of time, the PSOG 235 uses less power than the camera 237). Additionally, in this embodiment, the threshold to which the EMV is compared is 40°/second. In this embodiment, the eye tracking system illustrated in FIG. 1 may save power as a result of reducing the bitrate at which the data is read from the camera 237 when the values calculated based on the measurements 236 of the reflections are indicative of the EMV exceeding the threshold of 40°/second.

Figure 3:
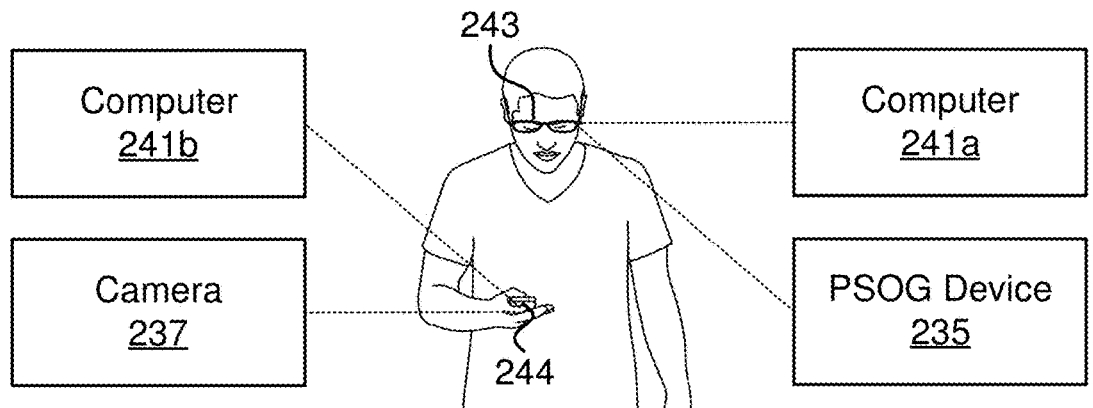
FIG. 3 illustrates eye tracking utilizing head-mounted PSOG and a non-head-mounted camera.

In another embodiment, the camera 237 may belong to a non-head-mounted battery-operated mobile device, reference to the computer 240 may involve, in this embodiment, at least a first component that is a head-mounted computer and a second component that is a non-head-mounted computer, which are configured to communicate over a wireless communication channel. In this embodiment, reducing the bitrate at which the data is read from the camera 237 when the values are indicative of the EMV exceeding the threshold may reduce power consumption of the non-head-mounted device. Such a scenario is illustrated in FIG. 3, where the camera 237 is embedded in a non-head-mounted battery-operated mobile device (a smartphone 244), while the PSOG 235 is part of a head-mounted device (smartglasses 243). Thus, in this example references to "the computer 240" may refer to a head-mounted computer 241a (e.g., a processor of the smartglasses 243) and/or a non-head-mounted computer 241b (e.g., a processor in the smartphone 244).

Given the importance of eye tracking for many applications, many systems include both PSOG and VOG components (e.g., the PSOG 235 and the camera 237, respectively), which are often used in a manner that is intended to improve performance tradeoffs. For example, the more power-demanding VOG may be utilized sporadically to correct and/or complement the less accurate but less power-demanding PSOG. One way in which PSOG and VOG may be utilized together is in the training and/or calibration of models for detecting eye movement and/or eye positions based on PSOG (e.g., determining eye positions based on the measurements 236 of the reflections). In some embodiments, data obtained from VOG (e.g., by analyzing the images taken by the camera 237) is utilized as a "ground truth" indicating eye movements and/or eye positions at the time the images were taken. This data can then be utilized to train a model (e.g., set parameters of the model) for power-efficient eye tracking that maps measurements of reflections obtained with PSOG to eye movements and/or eye positions.

In one embodiment, in order to train such a model, the computer 240 receives images captured by the camera 237 and calculates eye positions and/or eye movements based on analysis of the images (referred to herein as "image-based positions"). The image-based positions serve as labels (the ground truth) for training the model. Together with corresponding measurements of reflections measured at corresponding times with the PSOG 235, a training set of samples is generated. This training set is provided to a machine learning training algorithm and is used to train and/or update the model. In one example, the model may be a regression model. In another example, the model may include parameters of a convolution neural network. Additional details about how such models may be trained are provided in Rigas 2017.

In some embodiments, calibration approaches known in the art for determining eye positions based on PSOG may be adapted to some embodiments of the system illustrated in FIG. 1. For example, instead of obtaining ground truth positions by providing the user with cues indicating where to look, the approach described in Topal, et al. "A low-computational approach on gaze estimation with eye touch system." *IEEE transactions on cybernetics* 44.2 (2013): 228-239, can be adapted to use ground truth positions obtained determined based on images from the camera 237. In another example, eye positions can be determined based on images obtained by the camera 237 in a similar way to how ground truth positions are obtained with the IR camera in Li, et al. "Battery-free eye tracker on glasses." *Proceedings of the 24th Annual International Conference on Mobile Computing and Networking.* 2018.

The camera 237 may be operated at different times and/or at different frequencies in order to capture images that are utilized to calculate the image-based positions. For example, the camera 237 may be operated more when it is determined that a model used to calculate eye positions and/or eye movements based on PSOG may be inaccurate and/or may require calibration.

Each time a person wears the smartglasses there may be slight variations in the way the smartglasses fit on the face. These variations may involve slight sensor shifts, which can change the nature of the correlations between reflections measured with PSOG when the eye is at certain positions. In order to account for these variations, models used to calculate eye positions and/or eye movements based on PSOG may need to be updated and/or recalibrated. To this end, in some embodiments, when it is determined that the user put on the smartglasses 230, the camera 237 is operated in order to capture images that may be utilized as the ground-truth image-based positions.

In order to maintain accurate eye tracking results from the PSOG, in some embodiments, the camera 237 may be periodically be operated to capture images that are utilized as a ground truth according to which the accuracy of eye positions determined based on measurements of the PSOG 235 is evaluated. For example, camera 237 may be operated every few seconds and/or after certain events (e.g., after intense head movements are detected). Optionally, if the accuracy of the eye positions that are determined based the PSOG 235 falls below a certain threshold, then the camera 237 is operated at a higher frequency in order to provide additional images to serve for calibrating and/or retraining the model used to calculate the eye positions based on the measurements from the PSOG 235.

Extensive eye movements can be indicative of unrest of the user. In one embodiment, the computer 240 sums durations during which the EMV exceeded the threshold, and responsive to the sum reaching a second threshold, commands a user interface to present a calming message to the user (e.g., by displaying text with the message to the user or playing to the message via headphones worn by the user). In one example, the calming message may include an instruction to close the eyes and relax, or be a message that comes from a digital therapist application that is run in order to help the user to relax.

In one embodiment, the computer 240 utilizes at least one of the discrete photosensors utilized by the PSOG 235 to detect a flickering timing of ambient light, and set the camera 237 to capture the images 239 as a function of the flickering timing. For example, when capturing images during more light flickering periods improves the quality of the captured images, the computer may operate the camera according to the flickering timings in order to capture more images during the flickering periods.

In one embodiment, the PSOG 235 is mounted to a smartglasses frame comprising progressive ophthalmic lenses, and the computer is further configured to: receive an indication that the user is characterized as diabetic, detect, based on the values indicative of the EMV, shortening of averaged fixation periods, and command a user interface to suggest to the user to check his/her blood sugar level. The shortening of the averaged fixation periods may be indicative of diabetic retinopathy.

In another embodiment, the PSOG 235 is mounted to a smartglasses frame comprising progressive ophthalmic lenses, and the computer 240 is further configured to: receive an indication that the user suffers from dry eye syndrome, detect, based on the values indicative of the EMV, shortening of averaged fixation periods, and command a user interface to suggest to the user to treat the dry eye condition. The shortening of the averaged fixation periods may be indicative of the eye being too dry.

The following method may be used by systems modeled according to FIG. 1. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, emitting light and taking measurements of reflections of the light from an eye of a user by a photosensor-oculography device (PSOG).

In Step 2, capturing images of the eye measured in Step 1 by a camera. For example, the camera 237 may be utilized to capture such images.

In Step 3, calculating values indicative of eye movement velocity (EMV) based on the measurements of the reflections.

And in Step 4, reading data from the camera at a higher bitrate when the values are indicative of the EMV being below a threshold compared to when the values are indicative of the EMV being above the threshold.

In one embodiment, the method may optionally include the following steps: detecting, based on the values indicative of the EMV, eye fixations, smooth pursuit eye movements, and saccades, and reading the data from the camera at different bitrates during the eye fixations, the smooth pursuit, and the saccades. Optionally, average bitrates at which the data is read from the camera during the eye fixations and the smooth pursuit eye movements are at least three times greater than an average bitrate at which the data is read from the camera during saccades.

In another embodiment, the method may optionally include the following steps: calculating eye positions and/or eye movements based on analysis of the images (image-based positions), generating labels based on the image-based positions, generating feature values based on the measurements of the reflections, and providing the labels and feature values to train a machine learning-based model for detecting eye positions and/or eye movements based on additional measurements of reflections.

Some embodiments described herein involve calculation of the pupil features 246 based on the images 239 taken by the camera 237. Pupil features of an eye that appears, at least in part, in images may include one or more of the following types of values: a pupil center location, a pupil contour, a pupil diameter, glint location, a glint-pupil vector, a Haar-like feature, a result of an ellipse fitting approach, and a result of pupil edge filtering. The aforementioned pupil features are well known in the art, and discussed in the reference Fuhl, Wolfgang, et al. "Pupil detection for head-mounted eye tracking in the wild: an evaluation of the state of the art" Machine Vision and Applications 27.8 (2016): 1275-1288, which is incorporated herein by reference.

One advantageous aspect of some of the embodiments described herein is that they enable calculation of the pupil features in a power-efficient way by selectively choosing when to calculate the pupil features at a higher rate. For example, the pupil features may be calculated when they are more likely to be informative and/or accurate (e.g., at times in which the eye is relatively stationary). Optionally, determining when pupil features are more likely to be accurate and/or informative is done based on the values indicative of eye movement velocity (EMV), which are calculated based on the measurements 236 of the reflections.

Thus, in some embodiments, the computer 240 may be configured to obtain the images 239, and/or calculate the pupil features 246, at a higher rate during periods of eye fixations compared to periods of saccades. This can be beneficial because, on average, images captured when there are no saccades are sharper than images captured during saccades (which may be blurry and/or include artifacts due to the high velocity the eye's movements).

In one embodiment, the computer 240 calculates the pupil features 246 during eye fixations at a rate that is at least three times higher than a rate at which the pupil features 246 are calculated during saccades.

In another embodiment, the computer 240 sets timing of the camera 237 to capture above 80% of the images when the values are indicative of the EMV being below the threshold. For example, the computer 240 may decrease the frequency at which the camera 237 captures images, or refrain from capturing images altogether, when the values calculated based on the measurements 236 of the reflections are indicative of the EMV being above the threshold. Optionally, having the EMV be above the threshold is indicative of saccades (i.e., that the eye is performing saccadic movements).

In yet another embodiment, the computer 240 identifies saccades based on the values calculated based on the measurements 236 of the reflections. The computer 240 utilizes identifications of saccades for timing the camera to capture above 80% of the images when there are no saccades.

Identifying whether the eye is in the midst of saccadic movements may be done in different ways. In some embodiments, if the values calculated based on the measurements 236 of the reflections are indicative of the EMV reaching a threshold, this may be interpreted by the computer 240 as an occurrence of a saccade (i.e., the eye is performing a saccadic movement). In other embodiments, the computer 240 may utilize a machine learning-based approach to identify a saccade. For example, the computer 240 may generate feature values based on the measurements 236 of the reflections, and utilize a model to calculate, based on the feature values a certain value indicative of whether the user's eye is in a saccade movement. Optionally, if the certain value indicates that the probability that the eye is in a saccade is above a certain threshold, then then the computer 240 reduces the frequency at which the camera 237 captures images or has the camera 237 refrain from capturing images for a certain period (e.g., a few tenths of a second) and/or until the certain value, when calculated based on later measurements of reflections, indicates that the eye is no longer in saccade movement. Optionally, the feature values may include values indicative of extents of reflections at different times (e.g., raw values measured by the PSOG), and/or various values that may be functions of these values, such as volume local binary patterns (VLBP), cuboids, and/or optical strain-based features. Optionally, the model utilized to calculate the certain value is trained based on data comprising previous measurements of reflections of the eye of the user measured by the PSOG 235 and previous images of the eye of the user captured with the camera 237. To train the model, feature values were generated based on the previous measurements, and labels indicative of whether the user's eye was in a saccade movement were generated based on the previous images using techniques known in the art for identifying saccade movements. In one example, the model may include parameters of a regression model (e.g., a linear regression model or a logistic regression model). In another example, the model may include parameters of a convolution neural network.

During periods of saccades there is often less visual processing performed by the brain. Thus, certain pupil features, associated with visual processing, can be less informative, and/or provide less utility, during periods of saccades. Therefore, in some embodiments, the computer 240 identifies saccades based on the values calculated based on the measurements 236 of the reflections, and calculates the pupil diameter, based on the images 239, at a higher rate during periods without saccades compared to periods of saccadic movements.

In some embodiments, due to optical design of the camera 237 and/or the location of the camera 237 relative to the eye, images of the pupil are sharper when a gaze direction of the user is in a first direction compared to when the gaze direction of the user is in a second direction. Optionally, the first and second gaze directions differ by at least 20°. Optionally, the first and second gaze directions differ by at least 45°. In one embodiment, the computer 240 calculates an eye position based on the measurements 236 of the reflections. Optionally, the eye position is indicative of a direction of the user's gaze, which is indicative of whether the gaze is closer to the first direction than it is to the second direction. Knowing the gaze direction can enable saving power. For example, the computer 240 can calculate the pupil features more frequently based on images taken while the gaze direction is in the first direction, compared to images taken while the gaze direction is in the second direction.

In one embodiment, the computer 240 calculates the eye position based on the measurements 236 of the reflections at a rate that is at least ten times higher than a rate at which the pupil features 246 are calculated based on the images 239. This difference in the rate of calculating the eye position based on the measurements 236 of the reflections versus the rate of the calculating the pupil features 246 based on the images 239 can further reduce the power consumption of the system.

Utilizing the PSOG 235 to determine when, and/or to what extent, to calculate pupil features can be advantageous when the camera 237 and/or the computer 240 are battery-operated, such as when these components are embedded in a wearable device (e.g., smartglasses) or a mobile device (e.g., a smartphone).

In one embodiment, the camera 237 belongs to a non-head-mounted battery-operated mobile device, and "the computer 240" comprises a head-mounted computer and a non-head-mounted computer, which are configured to communicate over a wireless communication channel. Reducing the rate at which the pupil features 246 are calculated, when the values are indicative of the EMV exceeding the threshold, can save power expenditure of the non-head-mounted device. For example, the head-mounted computer may be embedded in smartglasses, the non-head-mounted computer may be embedded in a computer smartphone, the camera 237 may be the front-facing camera of the smartphone, the smartphone may run an eye tracker, and the wireless communication channel may be Bluetooth Low Energy. In this embodiment, the threshold to which the EMV is compared may be selected to exclude saccades. For example, reaching the threshold indicates that a probability that the eye is in a saccadic movement is at least a certain probability, and the certain probability is greater than 50%. FIG. 3 illustrates such an embodiment. This example reduces the power consumption of running the eye tracker on the smartphone 244 by making it unnecessary for the smartphone's eye tracker to attempt to calculate pupil features during saccades. One example of a smartphone eye tracker, which can be adapted to save power by refraining from analyzing images taken during saccades, is the multi-layer feed-forward convolutional neural network eye tracker disclosed in the reference Valliappan, Nachiappan, et al. "Accelerating eye movement research via accurate and affordable smartphone eye tracking" Nature communications (2020).

Variations due to flickering ambient light can affect the quality of pupil features calculated based on the images 239. Thus, in some embodiments, the computer 240 is configured to utilize at least one of the discrete photosensors utilized by the PSOG 235 to detect a flickering timing of ambient light, and adjust periods during which the light is emitted by the PSOG 235 according to the flickering timing of the ambient light. Optionally, timing the periods during which the light is emitted by the PSOG 235 according to the flickering timing of the ambient light improves the signal-to-noise ratio of the measured reflections, which improves the computer's ability to calculate the eye-related parameters based on measurements of reflections measured by the PSOG 235. Additionally or alternatively, timing the periods at which the PSOG 235 emits light can help to provide more consistent illumination to images captured during those times, which can assist in improving the quality of pupil features calculated based on the images captured at those times.

In one example, the periods during which the light is emitted are timed by the computer 240 to coincide with periods between the flickering of the ambient light. In another example, the periods during which the light is emitted are timed by the computer 240 to coincide with periods of low intensity ambient light from a flickering ambient light source.

The following method may be used by systems modeled according to FIG. 1. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, emitting light and taking measurements of reflections of the light from an eye of a user by a photosensor-oculography device (e.g., the PSOG 235).

In Step 2, capturing images of the eye measured in Step 1 by a camera. For example, the camera 237 may be utilized to capture such images.

In Step 3, calculating values indicative of eye movement velocity (EMV) based on the measurements of the reflections.

And in Step 4, calculating pupil features, based on the images, at a higher rate when the values calculated in Step 3 are indicative of the EMV being below a threshold compared to when those values are indicative of the EMV being above the threshold.

In one embodiment, having EMV below a first threshold is indicative of an eye fixation and having the EMV above a second threshold is indicative of a likely saccade. In this embodiment, the pupil features are calculated during eye fixations (i.e., when the values calculated in Step 3 are below the first threshold) at a rate that is at least three times higher than a rate at which the pupil features are calculated during saccades (i.e., when the values are above the second threshold).

The values calculated in Step 3 may be utilized in various ways to determine when and/or to what extent images are captured by the camera. Thus, fewer images may be captured when pupil features calculated based on the images are likely to be less accurate and/or less informative.

In one embodiment, the method described above also includes a step that involves utilizing the values indicative of the EMV in order to operate the camera at a higher frame rate when the values are indicative of the EMV being below the threshold compared to when the values are indicative of the EMV exceeding the threshold.

In one embodiment, the method optionally includes a step of setting timing of the camera to capture above 80% of the images when the values are indicative of the EMV being below the threshold. The fact that the EMV is above the threshold may be indicative of saccades, and on average, images captured when there are no saccades are sharper than images captured during saccades.

In another embodiment, the method optionally includes a step of identifying saccades based on the values, and utilizing identifications of the saccades for timing the camera to capture above 80% of the images when there are no saccades.

In yet another embodiment, the method optionally includes a step of identifying saccades based on the values, and calculating the pupil diameter, based on the images, at a higher rate during periods without saccades compared to periods of saccadic movements. It is noted that here is less visual processing during saccades and therefore it is less valuable to measure changes in pupil diameter during saccades.

Figure 4:
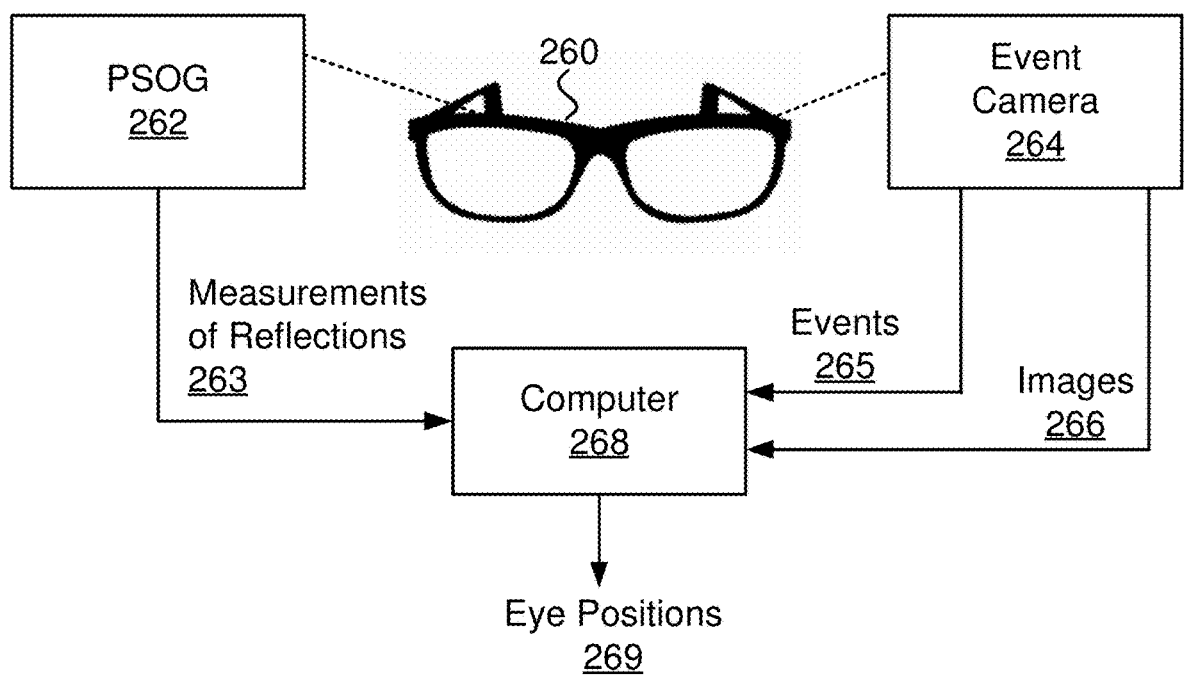
FIG. 4 illustrates an embodiment of an eye tracking system that utilizes an event camera.

FIG. 4 illustrates an embodiment of an eye tracking system that utilizes an event camera. In some embodiments, the system includes at least a photosensor-oculography device (PSOG 262), which is configured to emit light and to take measurements 263 of the reflections of the light from an eye of a user, an event camera 264 that is configured to capture the eye and to provide events 265, and a computer 268 that calculates positions of the eye (eye positions 269) based on the events 265 and the measurements 263. Optionally, one or more components of some embodiments of the system illustrated in FIG. 4, such as the PSOG 262, the event camera 264, and/or the computer 268 may be head-mounted and/or coupled to (and/or embedded) in frames of smartglasses 260 that are configured to be worn on the user's head.

It is to be noted that "capturing the eye" by the event camera 264 refers to taking measurements resulting from capturing (detecting) photons reflected from the eye, these can result in the events 265 and/or frame images 266 (which are discussed below).

Due to the nature of how the signals are acquired, the measurements 263 of the reflections and the events 265 will often be received in different manners. Namely, the events 265 are typically detected asynchronously, while the measurements 263 may be obtained in a synchronous manner (e.g., during certain periods, the PSOG 262 may be operated at a fixed frequency at which it emits lights and measures reflections from the eye). Additionally, due to the nature of the operation of event cameras, which enable a quick reading of single pixels, in some embodiments, the rate at which the events 265 are received can be higher than the rate at which the measurements 263 are acquired. Utilizing both the measurements 263 and the events 265 to calculate the eye positions 269 can leverage the different characteristics of these signals to improve performance of an eye tracker system that utilizes the PSOG 262 and the event camera 264, in terms of accuracy, frequency, and/or reduced power usage. The following is a description of some of the ways in which the measurements 263 of the reflections and the events 265 may be utilized by the computer 268 in order to calculate the eye positions 269, which may confer some of the aforementioned advantages.

One approach that may be utilized by the computer 268, relies in the fact that in some embodiments, the event camera 264 is able to generate events at a much higher rate compared to the rate at which the PSOG 262 operates. In these embodiments, the computer 268 may use the measurements 263 to calculate eye positions (referred to herein as "main eye positions") and use the faster occurring events 265 to update the eye positions at times that fall between consecutive main eye positions calculated based on the measurements 263 (these updated eye positions, which are calculated based on the events 265 are referred to herein as "intermediate eye positions"). Thus, the eye positions 269 may include a stream of positions that combines both the main eye positions, calculated from the measurements 263 obtained from the PSOG 262, and the intermediate eye positions, calculated by updating the main eye positions according to events detected by the event camera 264, which were detected in between the times corresponding to the main eye positions. Optionally, the computer 268 calculates, based on the measurements 263 a stream of main eye positions, and calculates based on the events 265 intermediate streams of eye positions which are located between at least some of the main eye positions. Optionally, on average, time that elapses between calculation of consecutive eye positions in the intermediate streams is much shorter than average time that elapses between calculation of consecutive eye positions from among the main eye positions.

The main eye positions calculated based on the measurements 263 may include a parametric representation of the eye. One example of a parametric representation is described in the reference Angelopoulos, et al., "Event Based, Near Eye Gaze Tracking Beyond 10,000 Hz" arXiv preprint arXiv:2004.03577 (2020). Angelopoulos, et al. describe how image data can be utilized to represent an eye position using a model with 13 parameters describing properties that include parameters of an ellipse representing the pupil, a parabola representing the eyelashes, and a circle representing the glint (a reflection of an IR light source off of the user's eyeball). The parameters are fit based on data obtained from images, and updated incrementally based on events. In a similar fashion, the computer 268 may fit parameters of a model of the eye based on the measurements 263 to obtain the main eye positions, e.g., using one or more of the standalone PSOG eye tracking approaches mentioned herein. These main eye positions can then be updated based on the events 265 in a similar fashion to the updating of eye positions described in Angelopoulos, et al.

Thus, the resulting calculations performed by the computer 268 can be viewed, in some embodiments, as a fusion algorithm that combines between the measurements 263 and the events 265. In one embodiment, this fusion algorithm includes the following steps: In step 1, set an initial eye position based on a subset of the measurements 263 taken a time t. In step 2, receive a subset of the events 265 that were detected after the time t and calculate updated eye positions by adding shifts obtained from these events to the initial eye position, until new measurements of reflections are received at time t+Δ. And in step 3, go back to step 1 to set the initial eye position based on the measurements of reflections received at t+Δ.

It is to be noted that due to the speed at which events are detected, an eye tracker that utilizes a fusion approach, as described above, may achieve a very high tracking frequency. For example, in some embodiments, the PSOG 262 may operate at a frequency of 200 Hz or even 1000 Hz. However, with the combination of updating eye positions using the events 265, the tracker is capable of providing eye positions at a frequency of 10,000 Hz or more.

Another approach that may be utilized by the computer 268 in the calculation of the eye positions 269 involves selection of which data from the different devices to use (from among the measurements 263 and the events 265) based on which is appropriate at a given time, according to a detected behavior of the eye. This may save power and/or increase accuracy of eye tracking.

In one embodiment, the computer 268 operates the event camera 264 in a normal mode while eye movement velocity (EMV) is above a threshold, and operates the event camera 264 in a low-power mode during fixations (which, for example, may cause it to detect fewer events) or refrains from processing the events 265 during the fixations. Optionally, the computer 268 calculates the eye positions 269 based on the measurements 263 during the fixations. Optionally, the computer 268 calculates the EMV based on the measurements 263, e.g., as discussed above with reference to calculations of the EMV by the computer 240 based on the measurements 236 of the reflections. It is to be noted that the threshold mentioned with respect to the EMV that is calculated based on the measurements 236 need not be the same threshold mentioned herein that relates to the EMV that is calculated based on the measurements 263.

In one embodiment, the computer 268 operates the PSOG 262 in a normal mode during fixations, and detects when the EMV reaches the threshold based on the measurements 263. Optionally, the computer 268 operates the PSOG 262 in a low-power mode when the EMV is above the threshold, and calculates the eye positions 269 based on the events 265 while the EMV is above the threshold.

Herein, a low-power mode for PSOG is a mode in which, over a certain period of time, the PSOG consumes less power than it would were it to operate in a normal mode. Optionally, power consumption of PSOG in the low-power mode is less than 50% of the power it consumes when operating in the normal mode. In some embodiments, achieving the lower power consumption of the low-power mode may involve one or more of the following: refraining from emitting and/or measuring reflections by the PSOG, reducing the frequency at which measurements are taken with the PSOG, reducing the extent of illumination by emitters of the PSOG, reducing the number of emitters of the PSOG that are operated, and/or reducing the number of discrete photosensors of the PSOG that are read.

In some embodiments, the total power consumed by the event camera 264 is higher than the total power consumed by the PSOG 262 (when operated in a normal operation mode for the same duration of time). Therefore, an eye tracker system that is based on these two components can save power by calculating the eye positions 269 based on measurements of the PSOG 262 (possibly without using events detected by the event camera 264) when the EMV is below the threshold, and calculating eye positions based on events 265 measured by the event camera 264 (possibly without using the measurements taken by PSOG 262) when the EMV is above the threshold.

The threshold for the EMV may be selected according to one or more of the following considerations: (i) performances, accuracy, and/or delay of eye positions calculated by the PSOG 262 as a function of the EMV, (ii) performances, accuracy, and/or delay of obtaining eye positions calculated by the event camera 264 as a function of the EMV, and (iii) power consumption of the PSOG 262 vs power consumption of the event camera 264, as a function of the velocity of eye movements that are to be tracked. For example, the threshold for the EMV may be 100°/second for a system that operates the PSOG 262 at a relatively low frequency that is not designed to measure saccades. Alternatively, the threshold for the EMV may be 400°/second for a system that operates the PSOG 262 at a higher frequency that enables it to measure normal saccades.

Operating the PSOG 262 may introduce, in some scenarios, artifact events that may be detected by the event camera 264, which are due to the light emitted by the PSOG 262, and not, for example, because of movement of the eye. To reduce the effect of such artifacts and/or overcome the effects altogether, in some embodiments, the light emitted by the PSOG 262 is in a first spectrum band, the event camera 264 is configured to capture the eye at a second spectrum band, and the first and second spectrum bands are disjoint. In other embodiments, the PSOG 262 may emit light in a certain spectrum band, and the event camera 264 may be equipped with a filter that attenuates most of the light detected in the certain spectrum band. For example, the filter may attenuate more than 95%, more than 98%, or more than 99.9% of the light in the certain spectrum band. Thus, the PSOG 262 and the event camera 264 may be considered to operate in spectrum bands that are essentially disjoint. Having the PSOG 262 and the event camera 264 operate in disjoint or mostly disjoint spectrum bands, as described above, can reduce, and even possibly eliminate, the detection of the artifact events.

In some embodiments, the computer 268 may disregard events detected at times at which the PSOG 262 emits light to illuminate the eye. In other embodiments, the event camera 264 may refrain from generating events at times at which the PSOG 262 emits light to illuminate the eye.

In one embodiment, the event camera 264 is head-mounted, and a first range of eye positions trackable from the measurements 263 is broader than a second range of eye positions trackable from the events 265. Optionally, the computer 268 calculates at least some of the eye positions 269 based on the measurements 263 when the eye positions are outside the second range. Optionally, the computer 268 calculates at least some of the eye positions 269 based on the events 265 when the eye positions are within the second range. Optionally, the computer 268 does not utilize the measurements 263 to calculate the eye positions 269 when the eye positions are within the second range.

In some embodiments, the PSOG 262 and the event camera 264 may be utilized together to train and/or calibrate a model for detecting eye movement and/or eye positions based on measurements taken by PSOG. In some embodiments, data obtained from the event camera 264 (e.g., by analyzing images generated from the events detected by the event camera 264) is utilized as a "ground truth", indicating eye movements and/or eye positions at the time. This data can then be utilized to train a model (e.g., by setting parameters of the model) for power-efficient eye tracking that maps measurements of reflections obtained with PSOG 262 to eye movements and/or eye positions.

In one embodiment, in order to train such a model, the computer 268 calculates eye positions and/or eye movements based on analysis of events 265 (referred to herein as "event-based positions"). The event-based positions serve as labels (the ground truth) for training the model. Together with corresponding measurements of reflections measured at corresponding times with the PSOG 262, a training set of samples is generated. This training set is provided to a machine learning training algorithm and is used to train and/or update the model. In one example, the model may be a regression model. In another example, the model may include parameters of a convolution neural network. Additional details about how such models may be trained are provided in the reference Rigas 2017.

In some embodiments, calibration approaches known in the art for determining eye positions based on PSOG may be adapted to some embodiments of the system illustrated in FIG. 4. For example, instead of obtaining ground truth positions by providing the user with cues indicating where to look, gaze estimation may be performed to obtain a similar reference ground truth using one or more of the approaches of the references mentioned herein for gaze estimation from events detected by an event camera.

In one embodiment, the event camera 264 captures the frame images 266 of the eye at a rate that is significantly lower than a rate at which the measurements 263 of the reflections are measured by the PSOG 262. Optionally, the computer 268 processes the events 265, the measurements 263, and the frame images 266 concurrently. Concurrent processing of events and frame images captured by an event camera is described for example in the reference Angelopoulos, et al., "Event Based, Near Eye Gaze Tracking Beyond 10,000 Hz" arXiv preprint arXiv:2004.03577 (2020). Adding the PSOG-based eye positions (which are not incremental updates like the events) may improve the robustness of the model and may enable the event camera 264 to lower the rate of capturing the frame images 266. One example for the significantly lower frame rate includes an embodiment of a system in which the event camera 264 captures the frame images 266 at a rate of 5 Hz, which are combined with measurements of the PSOG 262 that operates at a rate of 1,000 Hz.

In one embodiment, the computer 268 operates the event camera 264 in a normal mode when the EMV is above a threshold and eyelids covering the eye are open, and operates the event camera 264 in a low-power mode while the eyelids are closed or refrains from processing the events 265 while the eyelids are closed. Optionally, the computer 268 detects opening of the eyelids based on the measurements 263. Additional details regarding how the computer 268 may detect opening and closing of the eyelids based on measurements of reflections obtained with PSOG are provided below in the discussion regarding embodiments illustrated in FIG. 10.

In one embodiment, the computer 268 utilizes the eye positions 269, which are calculated based on the events 265 and the measurements 263, for calibration in calculations of eye positions based on the measurements 263. Optionally, in this embodiment, calculating eye positions based on the measurements 263 consumes less power compared to calculating eye positions based on the events 265. Optionally, the events 265 are utilized to calculate ground truth eye positions using one or more of the computational approaches mentioned herein. These ground truth eye positions are used to generate labels for training samples for training and/or calibrating a model for determining eye positions based on measurements of reflections measured with PSOG, as discussed above.

The following method may be used by systems modeled according to FIG. 4. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, emitting light and taking measurements of reflections of the light from an eye of a user by a photosensor-oculography device (PSOG). For example, the PSOG 262 may be utilized in this step to obtain the measurements 263 of the reflections of the eye of the user.

In Step 2, capturing the eye and providing events by an event camera. For example, the event camera 264 may be utilized in this step to detect the events 265.

And in Step 3, calculating positions of the eye (referred to herein as "eye positions") based on the events and measurements of the reflections. For example, the computer 268 may be utilized in this step to calculate the eye positions 269 based on the measurements 263 and the events 265.

Calculating the eye positions in Step 3 based on the measurements of the reflections and the detected events may be done in different ways. In one embodiment, the method may optionally include a step involving utilizing the events to incrementally update eye positions calculated based on the measurements of the reflections. In another embodiment, the method may optionally include the following steps: calculating based on the measurements of the reflections a stream of main eye positions, and calculating based on the events intermediate streams of eye positions, which are located between at least some of the main eye positions. Optionally, on average, time that elapses between calculation of consecutive eye positions in the intermediate streams is much shorter than average time that elapses between calculation of consecutive eye positions from among the main eye positions.

In one embodiment, a first range of eye positions trackable from measurements of the reflections measured by the PSOG in step 1 is broader than a second range of eye positions trackable from the events detected by the event camera in Step 2, and the method includes a step of calculating the eye positions based on the measurements of the reflections when the eye positions are outside the second range.

In one embodiment, the method may optionally include the following steps: calculating eye positions and/or eye movements based on analysis of the events detected in Step 2 (referred to herein as event-based positions), generating labels based on the event-based positions, generating feature values based on measurements of the reflections (measured by the PSOG in Step 1), and providing the labels and feature values to train a machine learning-based model for detecting eye positions and/or eye movements based on measurements of reflections.

In one embodiment, the method may optionally include a step of capturing, by the event camera, frame images of the eye at a rate that is significantly lower than a rate at which the reflections are measured by the PSOG. Optionally, processing the events, measurements of the reflections, and the frame images is done concurrently.

In one embodiment, the method may optionally include the following steps: operating the event camera in a normal mode during saccades, operating the event camera in a low-power mode during fixations or refraining from processing the events during the fixations, and calculating the eye positions during the fixations based on the measurements of the reflections.

In one embodiment, the method may optionally involve operating the event camera in a normal mode during saccades, operating the event camera in a low-power mode while the eyelids are closed or refraining from processing the events while the eyelids are closed, and detecting opening of the eyelids based on measurements of the reflections.

Figure 5:
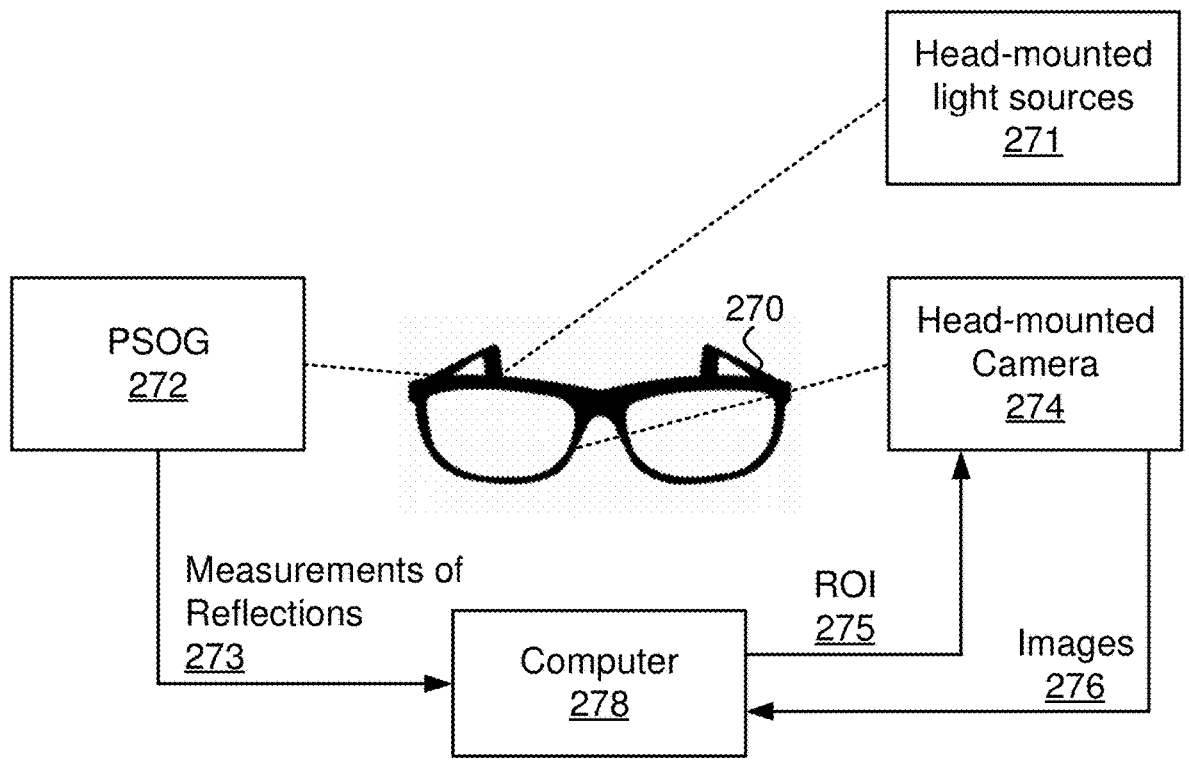
FIG. 5 illustrates an embodiment of an eye tracking system that includes PSOG and a camera that utilize a sensor that supports changing of its region of interest (ROI)

FIG. 5 illustrates an embodiment of an eye tracking system. In some embodiments, the eye tracking system includes a photosensor-oculography device (PSOG 272), a head-mounted camera 274, and a computer 278. The PSOG 272 is configured to emit light and to take measurements 273 of reflections of the light from an eye of a user. The head-mounted camera 274 is configured to capture images of the eye utilizing a sensor (i.e., an image sensor) that supports changing of its region of interest (ROI). Optionally, one or more components of some embodiments of the system illustrated in FIG. 5, such as the PSOG 272, the head-mounted camera 274, head-mounted light sources 271, and/or the computer 278 may be coupled to, and/or embedded in, frames of smartglasses 270 that are configured to be worn on the user's head.

The computer 278 calculates a position of the eye (also referred to herein as an "eye position") based on the measurements 273 of the reflections. The computer 278 then utilizes the calculated eye position to place an ROI 275 around pixels covering the eye's pupil, and reads the ROI 275 from the head-mounted camera 274. Optionally, reading the ROI 275 involves generation of images 276 that include the pixels covered by the ROI 275. Optionally, the images 276 do not include pixels that are not covered by the ROI 275, so for example, these pixels may be considered "captured" but not "read". Optionally, the ROI 275 covers less than 25% of the field of view of the sensor used by the head-mounted camera 274 (which is the sensor that supports the changing of its region of interest). Optionally, the ROI 275 covers less than 50% of the field of view of the sensor used by the head-mounted camera 274.

In some embodiments, to calculate the eye position, the computer 278 may utilize one or more of the techniques mentioned herein for calculating eye positions and/or eye movements based on the measurements of reflections obtained by PSOG, such as the techniques mentioned in Rigas 2017, Rigas 2018, and/or standalone PSOG approaches known in the art, such as the approaches mentioned further above in the references (i) Zemblys et al. (2018), (ii) Katrychuk et al. (2019), and/or (iii) Li et al. (2020).

In CMOS-based camera sensors, such as the image sensors that may be used by the head-mounted camera 274 in some embodiments, the term "region of interest" (ROI) may also be known as: window of interest readout, windowing, sub-windowing, region of interest readout, programmable region of interest, area of interest, partial readout window, random pixel access, and direct pixel addressing. In CCD-based camera sensors, the term region of interest may also be known as partial scanning For "a sensor that supports changing of its ROI", the changing of the ROI is a feature that allows reading only a portion of the pixels that were captured, and by that increasing the readout speed of the ROI, and optionally also reducing the camera's duty cycle. Some sensors also allow multiple ROI readouts in order to simplify the operation of multiple windowing. Sentences of the form of "set the ROI according to a subset of pixels", "to place the ROI around pixels covering an object", or "to place the ROI around pixels covering pupil of the eye" refer to setting the coordinates of the ROI to cover the "subset of pixels", "pixels covering an object", or "pupil of the eye", respectively. Herein, pixels are considered to "cover" a region/object if they are able to detect light reflected from that region/object.

The eye tracking system illustrated in FIG. 5 may be viewed as a video-oculography (VOG) system that utilizes photosensor-oculography (PSOG) in order to operate the camera used for the VOG more efficiently and thus be able to save power involved in eye tracking and/or increase the frequency at which images are acquired (due to the smaller number of pixels that needs to be read). Embodiments of the system illustrated in FIG. 5 may be utilized to implement different types of eye trackers, as discussed in more detail below. For example, the images 276 may be provided to an image-based eye-tracker that utilizes the images 276 to calculate various pupil features and/or a direction of gaze of the user.

In some embodiments, utilization of the eye position to place the ROI 275 around pixels covering the eye's pupil involves selecting, based on the eye position, a subset of pixels covering less than half field of view of the image sensor of the head-mounted camera 274, and setting the ROI 275 according to the subset. Various approaches may be utilized to select the pixels that will be covered by the ROI 275.

In one example, the eye position may be utilized to determine a certain region of pixels such as pixels that are a certain distance from a co-ordinate of the eye position). Optionally, the ROI 275 may be set to include a list of pixels that fall within the certain region. In another example, the ROI 275 is set according to co-ordinates of a bounding box that includes the eye position. Optionally, the eye position corresponds to the center of the bounding box or at a pre-determined location in the bounding box. Optionally, the bounding box has a predetermined size and/or location with respect to the eye position.

Figure 6:
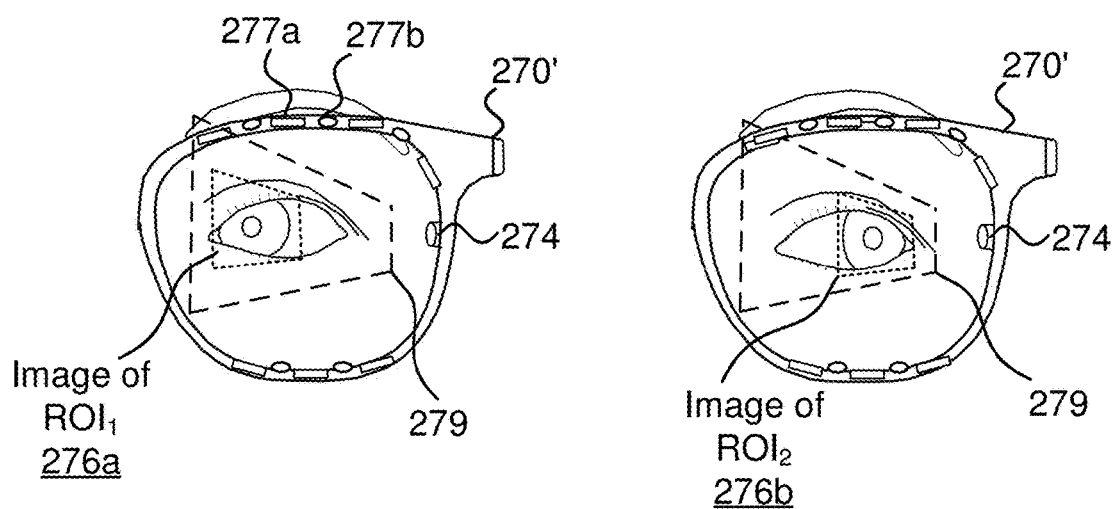
FIG. 6 illustrates a scenario in which different ROIs are read when the eye is at different eye positions.

FIG. 6 illustrates a scenario in which the system illustrated in FIG. 5 is used to read different ROIs when the eye is at different eye positions. The figure illustrates a portion 270' of the smartglasses frame 270 that includes the lens in front of the right eye. In this illustration, the PSOG 272 includes several emitters and discrete photosensors disposed in the portion 270' of the frame (e.g., photosensor 277a and emitter 277b). The head-mounted camera 274 takes images 279 that cover the area of the whole right eye. Note that the trapezoid shape of the images 279 is intended to illustrate possible distortions in the images due to the acute angle between the optical axis of the head-mounted camera 274 and the area of the eye. The eye position as calculated based on measurements of the reflections of the eye is used to change the ROIs read from the head-mounted camera 274. When the pupil is oriented outwards (i.e., when the user is looking to the right), as illustrated on the left side of FIG. 6, a first eye position is calculated and a first ROI (ROL) is set accordingly, and an image 276a of ROIs is read from the head-mounted camera 274. And when the eye moves, and the pupil is oriented more inwards, as illustrated on the right side of FIG. 6, a second eye position is calculated and a second ROI ($ROI_2$) is set accordingly, and an image 276b of $ROI_2$ is read from the head-mounted camera 274

Knowing the eye position can be utilized in some embodiments to identify locations of certain eye features referred to herein as "advantageous features" prior to capturing the images. These advantageous features may be useful for calculating various pupil features discussed herein. Some examples of advantageous features include pupil location, iris location, limbus location, and identification of locations of one or more glints that are expected to appear on the cornea from the camera's point of view. In some embodiments, the computer 278 is utilizes the eye position to select advantageous features before capturing the images 276. For example, locations of the advantageous features relative to the eye position are determined from evaluation of images (that are not restricted to the ROI 275) captured by the head-mounted camera 274. The computer 278 then sets the ROI 275 to cover the locations of advantageous features, and provides properties of said advantageous features to an image-based eye tracker (which may optionally involve the computer 278 performing calculations on the images 276).

Different positions of the eye expose to the camera different parts of the eye from different angles, which causes different features to have different quality levels for the VOG. The eyelid position and the lighting conditions also affect the efficiency and accuracy of VOG. Therefore, the computer 278 can utilize the PSOG's data (such as eye position, eyelid position, illumination) to select the advantageous features before capturing image, then set the ROI to capture the advantageous features, and then provide the properties of said advantageous features to the VOG tracker. The metric for selecting the advantageous features may depend on the expected accuracy to be obtained from analyzing the features (the higher the accuracy the better the feature is), and/or the expected required processing power to capture and/or analyze the feature (the lower the processing power the better the feature is).

In one embodiment, the image-based eye tracker comprises a limbus-based eye tracker and a glint-based eye tracker; switching between utilization of these two trackers is performed automatically based on the advantageous features that were selected, and a metric for selecting the advantageous features comprises at least one of expected accuracy to be obtained from analyzing the advantageous features and expected required processing power to capture and/or analyze the advantageous features.

Some implementations of eye trackers are based on detecting locations of glints in images that are caused when light from known light sources is reflected from the eye. For example, with VOG calculation the gaze direction can rely on the pupil-glint vectors, which are the relative distances between the centers of the pupil and one or more corneal reflections. The number of glints utilized, may depend on the number of light sources, and one example of an eye tracking process can be divided into two stages (i) analyzing the images to locate features, such as the glints and the pupil centers, and (ii) estimating the gaze based on the detected features.

There are various eye tracking approaches known in the art that rely on detecting glints (these systems are referred to herein as the glint-based eye trackers" mentioned above). One example for glint-based eye tracking is described in Mestre, et al., "Robust eye tracking based on multiple corneal reflections for clinical applications." *Journal of biomedical optics* 23.3 (2018): 035001. Additional examples of glint-based eye tracking are provided in Hosp, Benedikt, et al. "RemoteEye: An open-source high-speed remote eye tracker: Implementation insights of a pupil- and glint-detection algorithm for high-speed remote eye tracking." *Behavior research methods* 52.3 (2020).

In some embodiments, the system illustrated in FIG. 5 may be utilized to perform glint-based eye tracking. In these embodiments, head-mounted light sources 271 are configured to emit light that generates glints on the eye. The computer 278 utilizes the eye position (which is calculated based on the measurements 273 of the reflections) to select a subset of the head-mounted light sources 271 that are expected to generate one or more glints on the cornea. The computer 278 then operates the subset of the head-mounted light sources 271 at a higher intensity compared to the rest of the light sources. For example, the subset of the head-mounted light sources 271 can be selected based on the eye position calculated from the measurements 273, in such a way that when the eye position changes, the subset of the head-mounted light sources 271 may change accordingly (so they produce desired glints on the eye). It is noted that operating the subset of the head-mounted light sources 271 at a higher intensity compared to the rest of the head-mounted light sources 271 also refers to not operating the rest of the head-mounted light sources 271.

In some embodiments, the arrangement of the head-mounted light sources 271 and their operation (e.g., not all the light sources must be operated all the time) may have an effect on the glints that are generated. For example, different light sources may be interfered by the upper and/or lower eyelids as a function of the eyelid positions. The most suitable light sources to emit the light depend on both the eye tracker setup (which includes considerations such as the location of camera, the locations of the light sources, and the locations of the photosensors) and the properties of the user (which includes considerations such as the anatomical shape of eyelids, ethnicity, and age). Therefore, taking in account said considerations can have a significant impact on the performance of the eye tracker.

In one embodiment, the computer 278 calculates positions of the eyelids based on the measurements 273 of the reflections, and utilizes the positions of the eyelids to select a subset of the head-mounted light sources 271 that are expected to generate one or more glints on an area of the cornea not covered by the eyelids. The computer 278 then operates the subset of the head-mounted light sources 271 at a higher intensity compared to the rest of the light sources. Optionally, when the eye position changes, the calculations above are reperformed, and the subset of the head-mounted light sources 271 may change accordingly.

In another embodiment, the computer 278 calculates positions of the eyelids based on the measurements 273 of the reflections, and utilizes the positions of the eyelids to select a subset of the head-mounted light sources 271 that are not expected to be interfered by the eyelids and/or eyelashes, and/or expected to have a minimal interference with the eyelids and/or eyelashes. Such interference can cause light emitted from light sources not to form expected glints due to the at least some of the emitted light being absorbed by the eyelids and/or eyelashes. The computer 278 may then operate the subset of the head-mounted light sources 271 at a higher intensity compared to an intensity at which the rest of the light sources, from among the head-mounted light sources 271, are operated.

By knowing the location of the head-mounted camera 274, the locations of the head-mounted light sources 271, and the eye position, in some embodiments, the computer 278 estimates the locations of the glints on the cornea, and sets the ROI 275 to be around the cornea. Optionally, the properties of the ROI 275 are fed into the glint-based eye tracker that processes the ROI 275 in a similar manner to processing cropped images together with their cropping parameters, as is performed by some eye trackers known in the art. To this end, in one embodiment, the computer 278 calculates positions of the eyelids based on the measurements 273 of the reflections, utilizing the eye position and the positions of the eyelids to set the ROI 275 around the cornea, such that the ROI 275 covers an area that is not greater than two times the area of the eye that is not covered by the eyelids. The images 276 then can be provided for utilization of the glint-based eye tracker. In another embodiment, the computer 278 utilizes the eye position to set the ROI 275 around the cornea, such that the ROI 275 covers an area that is not greater than two times the area of a square that surrounds the iris tightly.

In one embodiment, the computer 278 operates an eye tracker that is based on detecting pupil contour. In this embodiment, the computer 278 utilizes the eye position to set the ROI 275 around the iris, such that the ROI 275 covers an area that is not greater than two times the area of a square that surrounds the iris tightly. Optionally, determining how to set the ROI 275 to include the iris is done using a model trained based on images captured by the head-mounted camera 274 (in which the pupil contour is detected and an appropriate square is positioned), as discussed above.

In another embodiment, the computer 278 operates an eye tracker that is based on detecting pupil contour. In this embodiment, the computer 278 estimates a location of the pupil based on the eye position, and utilizes the eye position to set the ROI 275 around the pupil, such that the ROI 275 covers an area that is not greater than two times the area of the eye that is not covered by the eyelids.

Some of the embodiments described herein involve calculating various eye-related features based on the eye position and/or the measurements 273 of the reflections, and then utilizing these features to determine operational parameters, such as selection of a subset of the head-mounted light sources 271 and/or selection of the ROI 275 so it conforms to a certain condition (like including certain features). Some examples of eye-related features that may be calculated for these purposes include detection of locations of the eyelids and/or eye lashes, calculation of a pupil location, an iris location, limbus location, and estimation of locations of one or more glints that are expected to appear on the cornea from the camera's point of view. These features are often more easily and/or accurately extracted from images (e.g., images taken by the head-mounted camera 274). However, as explained below, by using such images to train a machine learning-based model, it is possible to calculate values of these eye-related features, even at times at which images are not captured by the head-mounted camera 274, which can help conserve power (since the head-mounted camera 274 can be operated for shorter periods).

In some embodiments, eye positions and/or the measurements of the reflections obtained by the PSOG 272 (from which the eye positions are calculated) are an input to a function that calculates values of an eye-related feature, such as one or more of the eye-related features mentioned above. The calculation of the values of the eye-related feature may utilize, in these embodiments, a model that is trained with samples that each includes feature values that are generated based on an eye position and/or measurements used to calculate the eye position and a label generated from analysis of one or more images captured by the head-mounted camera 274 at the same time the measurements used to generate the feature values were taken. Examples of the feature values that may be generated by the computer 278 include co-ordinates of the eye position, dynamics of the eye position (e.g., changes to speed and trajectory), and various PSOG-related feature values that are known in the art mentioned in references described herein. Additionally, the computer 278 may generate feature values indicating which of the head-mounted light sources 271 were utilized in order to generate the measured reflections.

The labels are generated using image analysis techniques known in the art to detect the features that are to be calculated with the model, such as analyzing images to find the location of glints or positions of eyelids (which are more readily detected the images compared to the PSOG data).

Training samples that include the aforementioned features and labels are provided to a machine learning algorithm, such as an algorithm for training a regression model, a neural network, etc. This results in a personalized model that is capable of calculating eye-related features of the user based on measurements of the user obtained with the PSOG 272.

In one example, the computer 278 (i) extracts a set of eyelid positions based on analyzing the images 276, and (ii) provides labels that are based on the set of eyelid positions, and corresponding feature values that are based on the measurements 273 of the reflections, to train a model for calculating eyelid position based on additional measurements of the reflections obtained by the PSOG 272 (corresponding to times in which images are not captured by the head-mounted camera 274).

Since calculation of pupil feature may be computationally intensive, in some embodiments, the computer 278 my determine whether such a calculation is necessary prior to performing it. To this end, the computer 278 may calculate a correlation between a current image taken by the head-mounted camera 274 and a previous image having the same ROI 275 and eye position. If the correlation is above a certain threshold, the computer 278 retrieves a previously calculated value of a pupil feature when the correlation exceeds a threshold (i.e., use a "cached" value), or calculate a new value for the pupil feature based on the current image when the correlation is below the threshold.

The following method may be used by systems modeled according to FIG. 5. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, emitting light and taking measurements of reflections of the light from an eye of a user by a photo-sensor-oculography device (PSOG). For example, the PSOG 272 may be utilized in this step to obtain the measurements 273 of the reflections of the eye of the user.

In Step 2, capturing images of the eye by a head-mounted camera that utilizes a sensor that supports changing of its region of interest (ROI). For example, the head-mounted camera 274 may be utilized to capture the images in this step.

In Step 3, calculating, based on measurements of the reflections captured in Step 2, a position of the eye (referred to herein as an "eye position)".

In Step 4, utilizing the eye position for placing the ROI around pixels covering the eye's pupil.

And in Step 5, reading the ROI from the camera. Optionally, data read in this step is used calculate one or more pupil features.

In one embodiment, the method may optionally include the following steps: utilizing the eye position to select advantageous features before capturing the images, setting the ROI to cover the advantageous features, and providing properties of said advantageous features to an image-based eye tracker. Optionally, the advantageous features comprise data indicative of at least one of the following: pupil location, iris location, limbus location, and which glints are expected to appear on the cornea from the camera's point of view.

In another embodiment, the method may optionally include the following steps: (i) utilizing the eye position for selecting a subset of head-mounted light sources that are expected to generate one or more glints on the cornea (e.g., the head-mounted light sources 271), and (ii) operating the subset of the head-mounted light sources at a higher intensity compared to the rest of the light sources that are configured to emit light toward the eye.

In yet another embodiment, the method may optionally include the following steps: (i) calculating positions of the eyelids based on the measurements of the reflections, (ii) utilizing the positions of the eyelids for selecting a subset of the light sources that are expected to generate one or more glints on an area of the cornea not covered by the eyelids, and (ii) operating the subset of the light sources at a higher intensity compared to the rest of the light sources that are configured to emit light toward the eye.

In still another embodiment, the method may optionally include the following steps: calculating positions of the eyelids based on the measurements of the reflections, (ii) operating a glint-based eye tracker, and (iii) utilizing the eye position and the positions of the eyelids for setting the ROI around the cornea, such that the ROI covers an area that is not greater than two times the area of the eye that is not covered by the eyelids The approach of the eye tracking system illustrated in FIG. 5 may be expanded to involve additional types of sensors and/or devices (instead of PSOG or in addition to it) that provide information about the eye position. This information from the additional types of sensors and/or devices can then be utilized to operate a head-mounted camera that is part of the eye tracking system more efficiently by setting the ROI to a relevant region of the field of view of the head-mounted camera.

Figure 7:
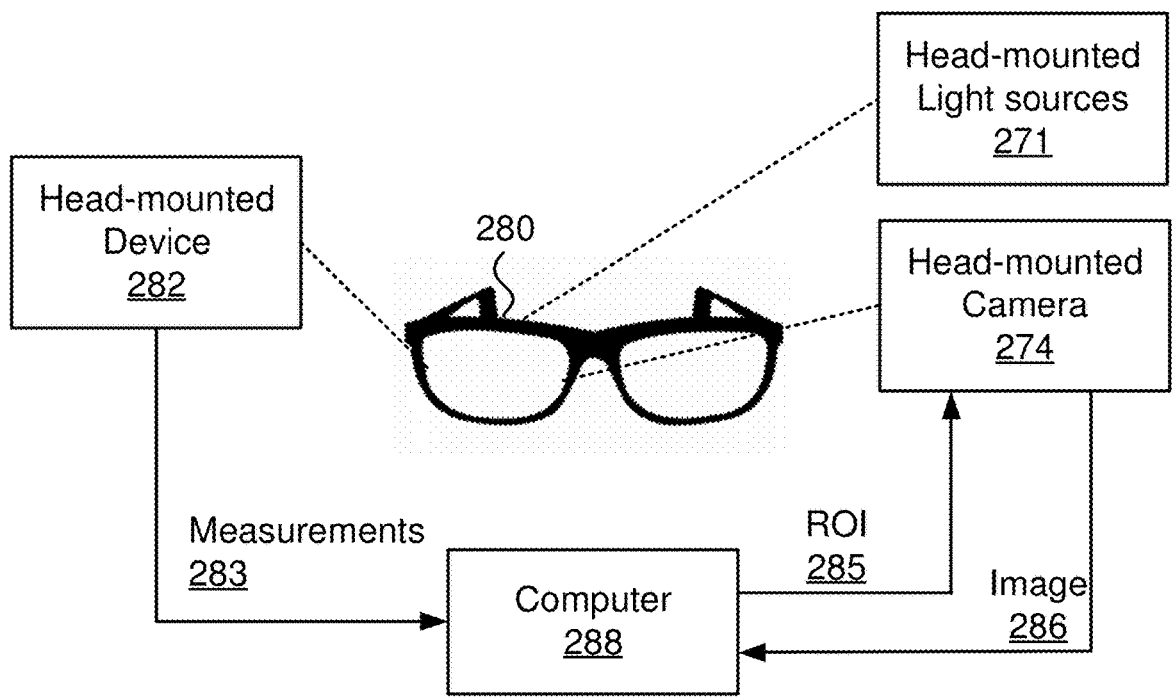
FIG. 7 illustrates an embodiment of an eye tracking system that utilizes measurements indicative of the eye position to set an ROI of a camera that captures images of the eye.

FIG. 7 illustrates an embodiment of an eye tracking system. In one embodiment, the eye tracking system includes a head-mounted device 282, the head-mounted camera 274, and a computer 288. The head-mounted device 282 takes measurements 283 that are indicative of a position of an eye of a user (referred to herein as "eye position"). The head-mounted camera 274 captures images of the eye utilizing a sensor (i.e., an image sensor) that supports changing of its region of interest (ROI). Optionally, one or more components of some embodiments of the system illustrated in FIG. 7, such as the head-mounted device 282, the head-mounted camera 274, the head-mounted light sources 271, and/or the computer 288 may be coupled to and/or embedded in frames of smartglasses 280, which are configured to be worn on the user's head.

The computer 288 calculates the eye position based on measurements 283. The computer 288 then utilizes the calculated eye position to place an ROI 285 around pixels covering the eye's pupil, and reads the ROI 285 from the head-mounted camera 274 (e.g., in order to obtain image 286 of the ROI 285). Optionally, the ROI 285 covers less than 30% of the field of view of the sensor used by the head-mounted camera 274 (which is the sensor that supports the changing of its region of interest). Optionally, the ROI 285 covers less than 50% of the field of view of the sensor used by the head-mounted camera 274.

To calculate the eye position based on the measurements 283, the computer 288 may utilize various approaches known in the art for determining the eye position which are appropriate for the type of sensors used in the head-mounted device 282 (as discussed below). Additionally or alternatively the computer 288 may utilize a machine learning-based approach, as discussed further below.

The head-mounted device 282 may include different types of components in embodiments described herein. These different components may provide different types of measurements indicative of the eye positions.

In one embodiment, the head-mounted device 282 includes an electrooculography (EOG) device, and measurements 283 include a value of an electrical potential between electrodes placed close to the eye. Calculating the eye position in this embodiment may involve various techniques known in the art for calculating eye position based on electrical potentials. Some examples of techniques that may be used by the computer 288 to calculate the eye position based on EOG data are described in Barea, Rafael, et al. "Wheelchair guidance strategies using EOG." *Journal of intelligent and robotic systems* 34.3 (2002): 279-299. In one example, a personalized machine learning-based model, which is trained based on images captured by the head-mounted camera 274 along with EOG measurements of the user taken at the same time, may be utilized to calculate the eye position, as discussed below. Embodiments in which the head-mounted device 282 include an EOG device can be used to implement a hybrid EOG-camera eye tracker, in which the eye position is calculated based on the electrical potential between the electrodes placed close to the eye.

In another embodiment, the head-mounted device 282 includes an electromyography (EMG) device, and the measurements 283 include a value of an electrical potential generated by muscle cells. Calculating the eye position in this embodiment may involve various techniques known in the art for calculating eye position based on electrical potentials. Some examples of techniques that may be used by the computer 288 in calculation of the eye position based on EMG data are described in Ahsan, et al., "EMG signal classification for human computer interaction: a review." *European Journal of Scientific Research* 33.3 (2009): 480-501, and in Monaco, A., et al. "Ocular correction effects on EMG activity of stomatognathic muscles in children with functional mandibular lateral-deviation: a case control study." *Eur J Paediatr Dent* 7.2 (2006): 81-8. In one example, a personalized machine learning-based model, which is trained based on images captured by the head-mounted camera 274 along with EMG measurements of the user taken at the same time, may be utilized to calculate the eye position, as discussed below. Embodiments in which the head-mounted device 282 includes an EMG device can be used to implement a hybrid EMG-camera eye tracker, in which the eye position is calculated based on the electrical potential generated by the muscle cells.

In yet another embodiment, the head-mounted device 282 includes an optical flow sensor, the measurements 283 include values of optical flow and/or visual motion, and the eye position is calculated using an optical flow algorithm known in the art. Some examples of techniques that may be used by the computer 288 in calculation of the eye position based on optical flow data are described in Jiménez-Pinto, et al., "Optical flow and driver's kinematics analysis for state of alert sensing." *Sensors* 13.4 (2013): 4225-4257. In one example, the optical flow sensor is an image sensor configured to measure optical flow and/or visual motion, and the motion of the eye is calculated based on an optical flow algorithm.

In still another embodiment, the head-mounted device 282 includes a range sensor, and the measurements 283 include values of a range (e.g., distance) between the range sensor and the eye. A range sensor may be a sensor configured to detect the presence of nearby objects without physical contact, such as a Doppler sensor, a passive optical sensor, an infrared sensor, a radar, and a sensor that measures time of flight. Since the eyeball is not perfectly spherical, the proximity between the range sensor at a fixed distance from the user's skull and the portion of the eyeball in the sensor's direct line-of-sight changes with eye movement. For example, the cornea is raised relative to the sclera, thus a shorter detected range may indicate that the cornea is in the sensor's direct line-of-sight. In one example, the eye position may be calculated utilizing a personalized machine learning-based model, which is trained based on images captured by the head-mounted camera 274 along with range measurements taken with the range sensor at the same time. Embodiments in which the head-mounted device 282 includes a range sensor can be used to implement a hybrid range-camera eye tracker that calculates the eye position based on the range between the range sensor and the eye.

In some embodiments, the head-mounted device 282 includes a PSOG configured to emit light and take measurements of the reflections of the light from the eye (e.g., the PSOG 272), and the eye position is calculated based on the measurements of the reflections.

Various embodiments described herein involve calculating the eye position based on the measurements 283, which may include different types of data, depending on the types of sensors and/or devices included in the head-mounted device 282 (e.g., EOG, EMG, PSOG, etc.). Determining the eye position can often be done accurately from analysis of images, such as images captured by the head-mounted camera 274. Additionally, determining the eye position from images at the same frequency as determined from the measurements taken by the head-mounted device 282 will typically be more power and computationally intensive than using the head-mounted device 282 alone. The fact that the head-mounted camera 274 and the head-mounted device 282 can be operated at the same time can be utilized to collect training data that can be used to calibrate models used to calculate eye position based on measurements taken by the head-mounted device 282, and thus achieve calculation of the eye position that is both accurate and power-efficient.

In some embodiments, measurements obtained from the head-mounted device 282 are an input to a function that calculates the eye position utilizing an eye position model. The eye position model is trained with samples that each includes feature values that are generated based on certain measurements obtained from the head-mounted device 282 at a certain time (e.g., features known in the art that are used to determine eye position from the specific type of data in the measurements), and a label indicative of the eye position at the certain time, as determined from analysis an image captured by the head-mounted camera 274 at the certain time. The labels are generated using image analysis techniques known in the art to detect the eye position.

Training samples that include the aforementioned features and labels are provided to a machine learning algorithm, such as an algorithm for training a regression model, a neural network, etc. This results in the eye position model being a personalized model that is capable of calculating eye position of the user based on measurements of the user obtained with the head-mounted device 282.

As discussed above, with respect to the computer 278, knowing the eye position can be utilized in some embodiments to identify locations of certain eye features, referred to herein as "advantageous features", prior to capturing an image with the head-mounted camera 274. In one embodiment, the computer 288 utilizes the eye position, which is calculated based on the measurements 283 that are indicative of the eye position, to select advantageous features before capturing the image 286. The computer 288 sets the ROI 285 to cover the advantageous features, and provides properties of said advantageous features to an image-based eye tracker. Optionally, the advantageous features include data indicative of at least one of the following: pupil location, iris location, limbus location, and which glints are expected to appear on the cornea from the camera's point of view.

In some embodiments, the system illustrated in FIG. 7 may be utilized to perform glint-based eye tracking. In these embodiments, the head-mounted light sources 271 are configured to emit light that generates glints on the eye. The computer 288 utilizes the eye position, which is calculated based on the measurements 283, to select a subset of the head-mounted light sources 271 that are expected to generate one or more glints on the cornea. The computer 288 then operates the subset of the head-mounted light sources 271 at a higher intensity compared to the rest of the light sources. For example, the subset of the head-mounted light sources 271 can be selected based on the eye position, in such a way that when the eye position changes, the subset of the head-mounted light sources 271 may change accordingly (so they produce desired glints on the eye). It is noted that operating the subset of the head-mounted light sources 271 at a higher intensity compared to the rest of the head-mounted light sources 271 (at a certain time) also refers to not operating the rest of the head-mounted light sources 271 (at the certain time).

In one embodiment, the computer 288 operates an eye tracker that is based on detecting pupil contour. In this embodiment, the computer 288 utilizes the eye position to set the ROI 285 around the iris, such that the ROI 285 covers an area that is not greater than two times the area of a square that surrounds the iris tightly. Optionally, determining how to set the ROI 2875 to include the iris is done using a model trained based on images captured by the head-mounted camera 274 (in which the pupil contour is detected and an appropriate square is positioned around iris), as discussed herein.

The following method may be used by systems modeled according to FIG. 7. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking, with a head-mounted device (e.g., the head-mounted device 282), measurements indicative of a position of an eye of a user (eye position).

In Step 2, capturing an image of the eye by a head-mounted camera that utilizes a sensor that supports changing of its region of interest (ROI). For example, the head-mounted camera 274 may be utilized to capture the image in this step.

In Step 3, calculating the eye position based on the measurements taken in Step 1.

In Step 4, utilizing the eye position for placing the ROI around pixels covering pupil of the eye.

And In Step 5, reading the ROI from the head-mounted camera.

Figure 8:
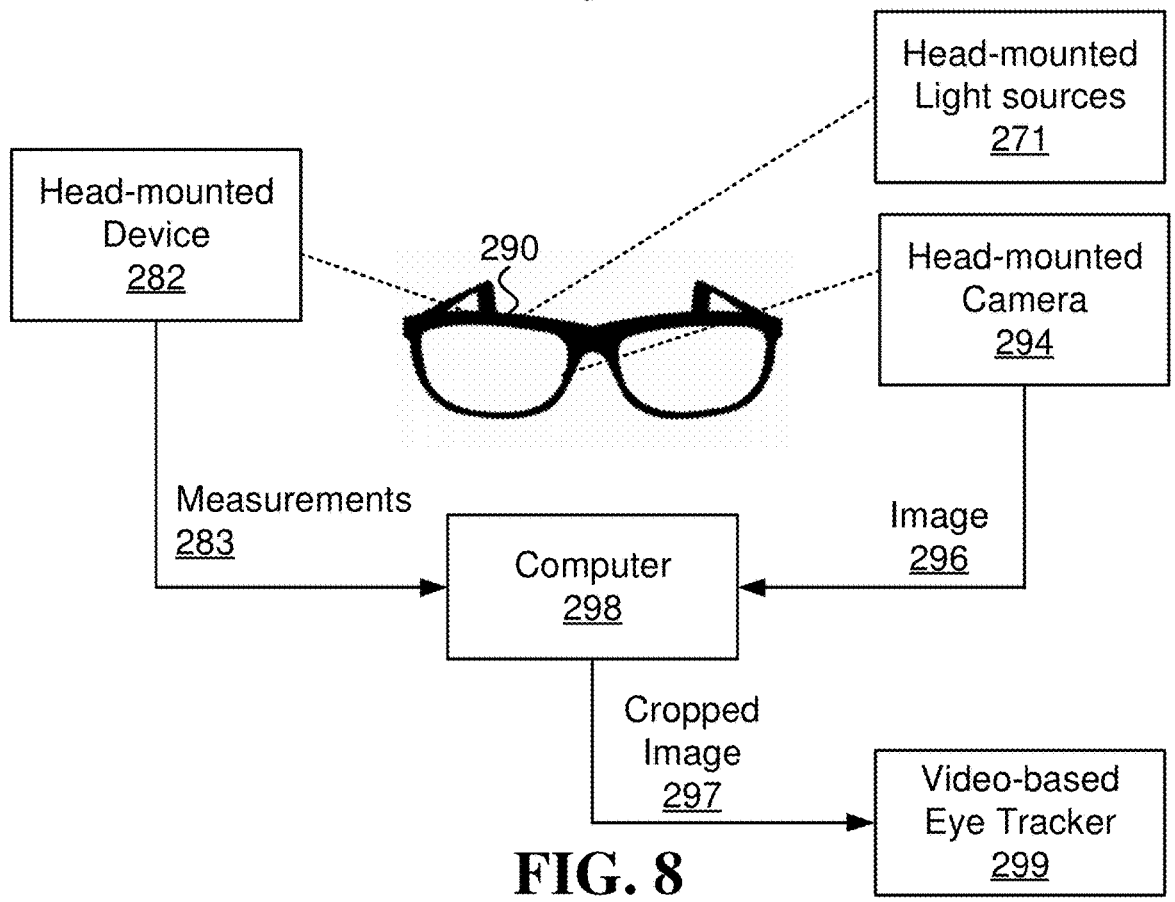
FIG. 8 illustrates an embodiment of an eye tracking system that utilizes measurements indicative of the eye position to crop an image of the eye.

Another way in which the eye position may be used to improve efficiency of eye tracking, especially with video-based eye trackers, is used by embodiments of eye tracking systems illustrated in FIG. 8. In some embodiments, an eye tracking system includes the head-mounted device 282, a head-mounted camera 294, and a computer 298. The head-mounted device 282 takes the measurements 283 that are indicative of a position of an eye of a user (referred to herein as "eye position"). The head-mounted camera 294 captures an image 296 of the eye of the user. Optionally, one or more components of some embodiments of the system illustrated in FIG. 8, such as the head-mounted device 282, the head-mounted camera 294, the head-mounted light sources 271, and/or the computer 298 may be coupled to and/or embedded in frames of smartglasses 290 that are configured to be worn on the user's head.

The computer 298 calculates the eye position based on the measurements 283 that are indicative of the eye position. The computer 298 then utilizes the calculated eye position to crop the image 296 around the pupil to produce cropped image 297, which is provided to a video-based eye tracker 299 (e.g., for more advanced eye tracking analysis). Optionally, the size of the cropped image 297 is less than a third of the size of its respective uncropped image (the image 296). Optionally, the cropped image 297 covers an area that is not greater than two times the area of a square that surrounds the iris tightly. Optionally, calculating the eye position based on the measurements 283 is performed at a rate that is at least ten times higher than the rate of capturing the image by the head-mounted camera 294. Optionally, when cropping the image 296, the computer 298 utilizes a similar approach to the one utilized for setting the ROI 275 or the ROI 285, discussed above. Namely, the computer 298 crops the image so it includes a sufficient margin, relative of the eye position, such that the cropped image 297 includes the pupil of the eye.

In one embodiment, the video-based eye tracker 299 calculate, based on the cropped image 297, at least one of the following values: a pupil diameter, and pupillary response. The term "pupillary response" refers to at least one of dilation response (widening of the pupil, also known as pupil dilation) and constriction response (narrowing of the pupil). To perform the calculation of the at least one of the pupil diameter and the pupillary response, the video-based eye tracker 299 may utilize one or more of the techniques known in the art for calculating pupil diameter and/or pupillary response from images of the eye.

As stated above in the discussion regarding embodiments of FIG. 7, the head-mounted device 282 may include different types of components, which is also the case in some embodiments of the system illustrated in FIG. 8, as described below. These different components may provide different types of values that are indicative of the eye positions that can be used by the computer 298 in order to produce the cropped image 297.

In one embodiment, the head-mounted device 282 includes a PSOG, the measurements 283 include measurements of reflections of light emitted by the PSOG towards the eye. Optionally the system further includes another PSOG that emits light and measures reflections of the light from the other eye of the user, and the system may also include another head-mounted camera that captures an image of at least a portion of the other eye of the user. Optionally, the head-mounted cameras may be part of a video oculography system.

In another embodiment, the head-mounted device 282 includes an electrooculography (EOG) device, the measurements 283 include a value of an electrical potential between electrodes placed close to the eye. In yet another embodiment, the head-mounted device 282 includes an electromyography (EMG) device, and the measurements 283 include a value of an electrical potential generated by muscle cells. In still another embodiment, the head-mounted device 282 includes an optical flow sensor, the measurements 283 include values of optical flow and/or visual motion, and the eye position is calculated using an optical flow algorithm known in the art. And in yet another embodiment, the head-mounted device 282 includes a range sensor, and the measurements 283 include a value of a range (e.g., distance) between the range sensor and the eye.

In some embodiments, the system illustrated in FIG. 8 may be utilized to perform glint-based eye tracking. In these embodiments, the head-mounted light sources 271 emit light that generates glints on the eye. Similarly to the computer 288, the computer 298 may utilize the eye position, which is calculated based on the measurements 283, to select a subset of the head-mounted light sources 271 that are expected to generate one or more glints on the cornea. The computer 298 then operates the subset of the head-mounted light sources 271 at a higher intensity compared to the rest of the light sources. Additionally or alternatively, the computer 298 may calculate positions of the eyelids based on the measurements 283. For example, the head-mounted device 282 may include a PSOG and the computer 298 may utilize the approach described with respect to the computer 278, which may calculate the positions of the eyelids based on the measurements 273 of the reflections. The computer 298 may then utilize the positions of the eyelids to select a subset of the head-mounted light sources 271 that are expected to generate one or more glints on an area of the cornea not covered by the eyelids, and operate the subset of the head-mounted light sources 271 at a higher intensity compared to the rest of the head-mounted light sources 271.

The following method may be used by systems modeled according to FIG. 8. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking, with a head-mounted device (e.g., the head-mounted device 282), measurements indicative of a position of an eye of a user (eye position).

In Step 2, capturing an image of the eye by a head-mounted camera (e.g., the head-mounted camera 294).

In Step 3, calculating the eye position based on the measurements taken in Step 1. Optionally, calculations of the eye position in this step are performed at a rate that is at least ten times higher than the rate at which images are captured by the head-mounted camera in Step 2.

In Step 4, utilizing the eye position to crop the image captured in Step 2 around the pupil.

And in Step 5, providing the cropped image to a video-based eye tracker.

In one example, the head-mounted device used in Step 1 includes a photosensor-oculography device (PSOG), and the measurements taken in Step 1 are of reflections of light emitted by the PSOG towards the eye.

In another example, the head-mounted device used in Step 1 includes an electrooculography device, and the measurements taken in Step 1 include a value of an electrical potential between electrodes placed close to the eye.

In yet another example, the head-mounted device used in Step 1 includes an electromyography device, and the measurements taken in Step 1 include a value of an electrical potential generated by muscle cells.

Figure 9A:
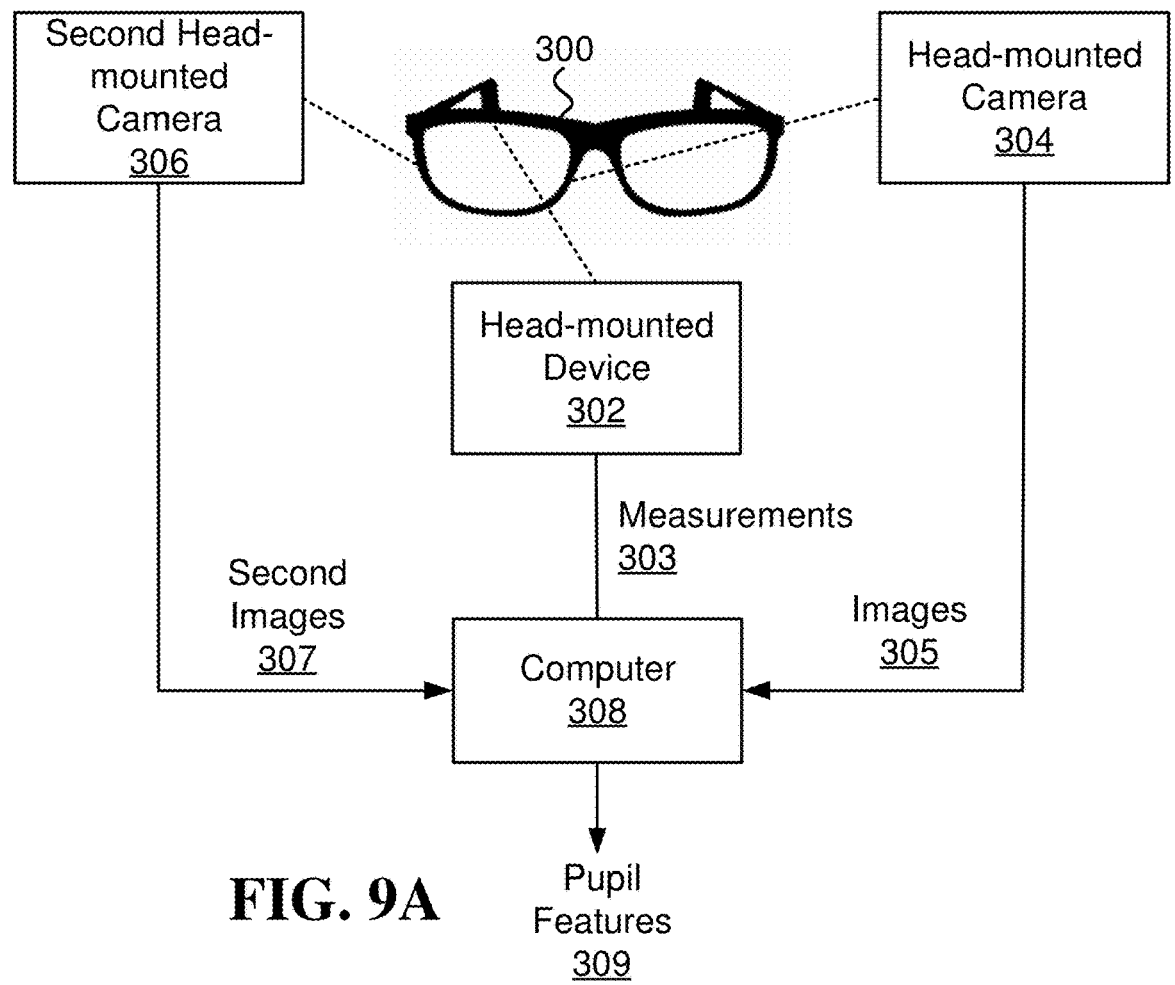
FIG. 9A illustrates an embodiment of an eye tracking system that operates a camera that captures images of the eye based on eye positions.

FIG. 9A illustrates an embodiment of an eye tracking system. In one embodiment, the eye tracking system includes a head-mounted device 302, a head-mounted camera 304, and a computer 308. The head-mounted device 302 takes measurements 303, which are indicative of positions of an eye of a user (referred to herein as "eye positions"). The head-mounted camera 304 captures images 305 of the eye. Optionally, a first range of eye positions trackable from the images 305 is narrower than a second range of eye positions trackable from the measurements 303. Optionally, one or more components of some embodiments of the system illustrated in FIG. 9A, such as the head-mounted device 302, the head-mounted camera 304, a second head-mounted camera 306, and/or the computer 308 may be coupled to and/or embedded in frames of smartglasses 300 that are configured to be worn on the user's head.

Herein, an eye position is considered "trackable", e.g., based on at least some of the images 305 and/or at least some of the measurements 303, if the respective source of data (aforementioned images and/or measurements) is sufficient in order for the computer 308 to determine the eye position. Optionally, an eye position is trackable from the source of data (aforementioned images and/or measurements) if the eye position is determined with a predetermined level of accuracy. Thus, certain eye positions that are not determined with the predetermined level of accuracy (e.g., because the eye may be gazing farther to one of the sided) are not considered trackable. In one example, an eye position is considered "trackable" if with probability of at least 95% the eye position is accurate within 1°.

Having the first range of eye positions be narrower than the second range may mean different things in different embodiments. In one example, the first range is contained in the second range; thus, every eye position that falls in the first range also falls in the second range, but there are at least some eye positions that fall in the second range do not fall in the first range (i.e., they are trackable with the measurements 303, but not in the images 305). In another example, each of the first and second ranges corresponds to a width of the field of view of the eye and/or each of the first and second ranges corresponds to a certain angular portion of the field of view. Optionally, the eye positions that fall outside the first range span at least 20° of the eye's field of view. In yet another example, each eye position may correspond to a vector describing the direction at which the pupil is pointed. In this example, having the first range be narrower that the second range may mean that when these directions are mapped to a surface of a unit sphere, the area on the face of the unit sphere that corresponds to eye positions in the first range is smaller than the area on the face of the unit sphere that corresponds to eye positions in the second range.

In one embodiment, the eye being tracked with the head-mounted device 302 is the right eye of the user, the head-mounted camera 304 is located to the right of the lateral canthus of the eye, and eye positions in vicinity of the medial canthus of the eye are outside the first range. For example, the eye positions in vicinity of the medial canthus, which are outside the first range, may span between 10° and 50°.

The computer 308 calculates the eye positions based on the measurements 303. The computer 308 then utilizes the calculated eye positions to determine how to read images from the head-mounted camera 304. In one embodiment, the computer 308 reads the images 305 from the head-mounted camera 304 at a first bitrate when the eye positions fall within the first range. The computer 308 may refrain from reading any images from the head-mounted camera 304, when the eye positions fall outside the first range. Alternatively, the computer 308 may read the images 305 from the head-mounted camera 304 at a second bitrate that is less than half the first bitrate, when the eye positions fall outside the first range.

In one embodiment, the computer 308 calculates the eye positions based on the measurements 303 at a rate that is at least ten times higher than a rate at which the images 305 are captured by the head-mounted camera 304. Optionally, the computer 308 may command the head-mounted camera 304 to operate in a low-power mode for a longer percent of time while the eye positions fall outside the first range, compared to a percent of time it operates in low-power mode while the eye positions fall within the first range.

In normal operation, the computer 308 may command the head-mounted camera 304 to operate in the low-power during at least some of the times the eye is in a position that falls outside the first range (e.g., an eye position that falls in the second range but not in the first range). The computer 308 may command the head-mounted camera 304 to exit the low-power when the eye is at a position that is in the vicinity of the first range of eye positions. This may optimize the power consumption by allowing the head-mounted camera 304 to remain in the low-power mode when the eye is not in a suitable position for the head-mounted camera 304 to capture useful images, and/or when the user and or the eye are in a situation in which there is a reduced need for images captured by the head-mounted camera 304. It is noted that if the head-mounted camera 304 has its own computer to decide when to operate in low-power mode, then the computer 308 referred to in this paragraph comprises two or more computers: one in the head-mounted camera 304 and another that operates the head-mounted camera 304 in addition to operating other components.

Having multiple head-mounted cameras can be beneficial in some embodiments; multiple head-mounted cameras can be used to provide images of the eye from different perspectives and/or when the eye is in different ranges of positions. Having this additional data can contribute, in some embodiments, to calculation of more accurate eye tracking values, such as gaze direction and/or pupil features and/or being able to calculate eye tracking values for a larger range of eye positions.

In some embodiments, the eye tracking system may include a second head-mounted camera 306 that captures a second set of images 307 of the eye (which is captured in images 305) from a different position than the head-mounted camera 304. Optionally, the computer 308 reads the second set of images 307 from the second head-mounted camera 306 at a higher bitrate when the eye positions fall outside the first range compared to when the eye positions fall within the first range. Optionally, the head-mounted camera 304 and the second head-mounted camera 306 are positioned at least 2 cm apart horizontally.

In one embodiment, the computer 308 commands the head-mounted camera 304 to operate in a low-power mode for a longer percent of time while the eye positions fall outside the first range compared to a percent of time it operates in the low-power mode while the eye positions fall within the first range. Additionally, the computer 308 commands the second head-mounted camera 306 to operate in a low-power mode for a longer percent of time while the eye positions fall within the first range compared to a percent of time it operates in the low-power mode while the eye positions fall outside the first range.

In another embodiment, the computer 308 may select which head-mounted camera, from among the head-mounted camera 304 and the head-mounted camera 306, to utilize based on an eye positions calculated based on the measurements 303. Optionally, the computer 308 utilizes a lookup table, which designates for different eye positions, which of the head-mounted cameras to utilize in order to capture images of the eye. Optionally, the computer 308 may detect that a sensor shift has occurred, due to at least one of the head-mounted camera 304 and the head-mounted camera 306 being in a different position and/or orientation. For example, such a shift may occur when these cameras are coupled to smartglasses 300, and the smartglasses 300 have moved due to the user removing them and putting them on again. Optionally, the sensor shift may be detected based on variations in the images 305 and/or the images 307 (e.g., detecting that certain facial landmarks appear at a different location and/or perspective). Additionally or alternatively, the sensor shift may be detected based on variations in the measurements 303 (e.g., using techniques mentioned herein with respect to sensor shifts with PS OG). Upon detecting the sensor shift, the computer 308 may update the lookup table, to reflect possible changes to ranges of eye positions best suited to be captured with each of the head-mounted cameras. For example, the computer 308 may change co-ordinates of the ranges (and which eye positions fall within them), based on specific parameters determined for the sensor shift (i.e., what change in location and/or orientation was determined for the sensor shift).

Figure 9B:
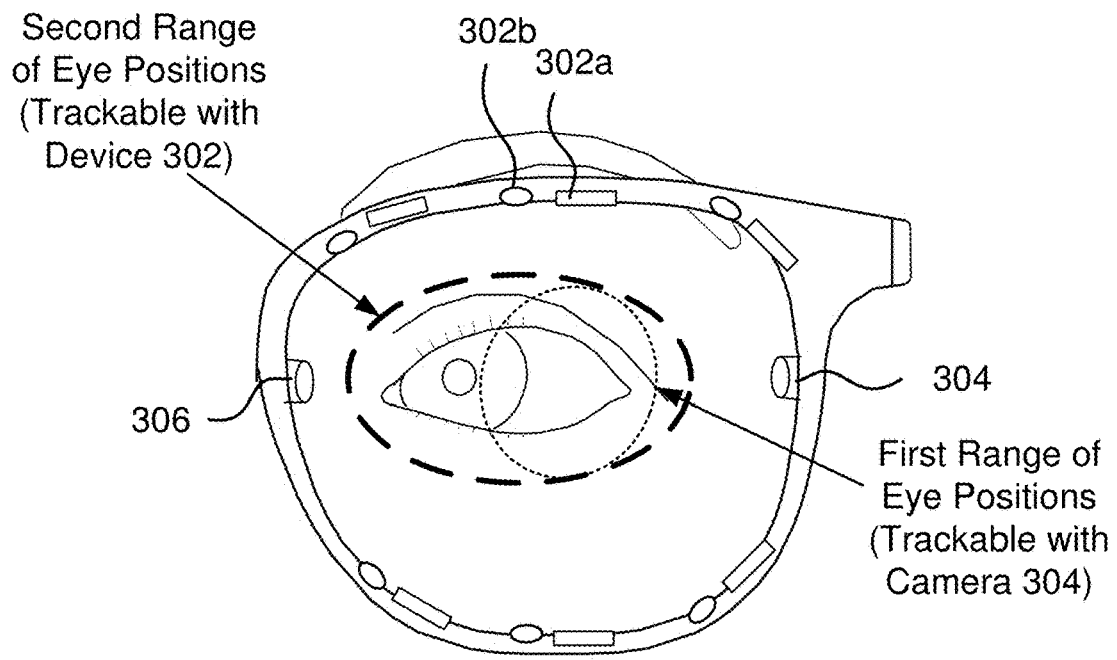
FIG. 9B illustrates an embodiment in which multiple head-mounted cameras are used for eye tracking.

FIG. 9B illustrates an embodiment in which multiple head-mounted cameras are used for eye tracking. The figure illustrates a portion of a smartglasses frame that is near the right eye of a user. The frame has embedded in it discrete photosensors (such as photosensor 302a) and emitters (such as emitter 302b) that provide measurements from which the computer 308 may determine the eye positions. The frame also has two head-mounted cameras coupled to it. The head-mounted camera 306 is located to the right of the eye and the head-mounted camera 304 is located to the left of the eye. The head-mounted camera 306 is better positioned to capture images of the user's pupil when the eye looks to the right, and the head-mounted camera 304 is better positioned to capture images of the user's pupil when the eye looks to the left.

In some embodiments, the head-mounted camera 304 and the second head-mounted camera 306 may be connected to the computer 308 over a bus that does not have sufficient bandwidth to transfer images from both cameras at a maximum bitrate at which the computer 308 is capable of reading from each of the cameras. Thus, the computer 308 may read at certain times, images at a higher bitrate from the camera that is better positioned to capture the pupil at a specific time.

In some embodiments, due to the positioning of the head-mounted camera 304 (e.g., when coupled to the frame of the smartglasses 300), there may be an acute angle between the focal plane of the head-mounted camera 304 and a plane representing the eye (e.g., the plane of the iris of the eye). Having an acute angle between these planes (e.g., an angle of less than 30°) may result in images captured by the head-mounted camera 304 being unclear. One corrective approach, which may be utilized in some embodiments, is to utilize the Scheimpflug principle, and have the head-mounted camera 304 configured such that its sensor is shifted relative to its optics (i.e., the focal plane). Optionally, the head-mounted camera 304 includes a mechanism that enables it to tilt and/or shift its sensor and/or its optics. For example, tilting and/or shifting the sensor and/or the optics of the head-mounted camera 304 may be done utilizing a piezoelectric motor and/or a microelectromechanical system (MEMS). Optionally, the computer 308 commands the head-mounted camera 304 to perform the tilting and/or shifting according to the eye positions. Optionally, the tilting and/or shifting based on the eye positions are done in order to obtain a certain angle between the sensor plane and the focal plane of the camera which is suitable for correcting, according to the Scheimpflug principle, image aberrations due to the acute angle between the head-mounted camera 304 and the iris plane of the eye when the eye is in a certain eye position. Optionally, the extent of the shifting and/or tilting performed when the eye is detected in the certain eye position is a predetermined according to calculations performed according to the Scheimpflug principle, which are known in the art. Optionally, the tilting and/or shifting comprises at least one of: tilting the sensor and/or the optics by an angle that is between 2.0° and 9°, and shifting the sensor and/or the optics by 1 to 3 mm.

In some embodiments, the head-mounted device 302 may include one or more devices of one or more types. In one embodiment, the head-mounted device 302 includes an electrooculography device, and the measurements 303 are indicative of electrical potentials between electrodes placed close to the eye. In another embodiment, the head-mounted device 302 includes an electromyography device, and the measurements 303 are indicative of electrical potentials generated by muscle cells. In another embodiment, the head-mounted device 302 includes an optical flow sensor, the measurements 303 are indicative of optical flow and/or visual motion, and the eye position is calculated using an optical flow algorithm. In still another embodiment, the head-mounted device 302 includes range sensors, and the measurements 303 are indicative of ranges between the range sensors and the eye.

In some embodiments, the head-mounted device 302 includes a photosensor-oculography device (PSOG), and the measurements 303 are of reflections of light emitted by the PSOG towards the eye. In some embodiments, designing the PSOG to have a wider tracking range compared to the first range trackable from head-mounted camera 304 can lead to a cost reduction. It may also lead to a weight reduction by enabling the system to capture each eye with a single camera located closer to the face than it would have been needed to be located had the head-mounted camera 304 had to capture a wider range of eye positions. In addition, the computer 308 can save power by lowering utilization of the head-mounted camera 304 when the eye is at an eye position in the second range (and not in the first range) compared to the utilization of the head-mounted camera 304 when the eye is at a position that falls in the first range.

In one embodiment, in which the head-mounted device 302 includes PSOG, the computer 308 utilizes a model to calculate the eye positions based on the measurements 303, which in this embodiment comprise measurements of reflections from the eye. As discussed elsewhere herein, e.g., in the discussion regarding the PSOG 235, this model may benefit from calibration. Optionally, calibration of the model may be done based on images captured by the head-mounted camera 304 when the first eye positions fall within the first range. Optionally, the model may be calibrated for eye positions that fall in the second range by extrapolating changes made to the model with eye positions in the first range. Optionally, the model may be calibrated for detecting eye positions that fall in the second range in the factory, or with a non-head-mounted VOG when the system has clear lenses that do not disturb the ability of the non-head-mounted VOG to collect the ground truth measurements required to calibrate the PSOG model.

In another embodiment, in which the head-mounted device 302 includes PSOG, the computer 308 utilizes a model to calculate the eye positions based on the measurements 303, which in this embodiment comprise measurements of reflections from the eye. Additionally, the computer 308 may utilize the images 305 (along with the measurements of the reflections) to calculate the eye positions. For example, utilizing both sources of data may result in more accurate calculations of eye positions than attainable when relying on only one of the sources of data. To calculate eye positions based on both sources of data, the computer 308 generates feature values based on data comprising measurements of the reflections and the images 305, utilizes a model to calculate the eye positions based on the feature values. Optionally, the feature values utilized are feature values described herein for the task of determining eye positions with PSOG and/or feature values known in the art for determining eye positions based on images.

In yet another embodiment, in which the head-mounted device 302 includes PSOG, the computer 308 extracts a set of eyelid positions based on analyzing the images 305. These extracted eyelid positions, along with measurements of reflections of light from the eyes taken by the PSOG at those times, can be utilized to train a model for calculating eyelid position based on additional measurements of reflections of light from the eye (e.g., taken at a future time for which there are no corresponding images). Optionally, the computer 308 generates training samples, each comprising feature values that are based on the emitted light and measurements of the reflections and a label based on the eyelid position at that time, and utilizes the training samples to train the model. Optionally, the computer 308 may generate feature values such as the ones described herein as being generated by the computer 278 for the purpose of calculating eyelid position and/or training a model for this purpose.

The following method may be used by some embodiments of systems modeled according to FIG. 9A. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking, with a head-mounted device (e.g., the head-mounted device 302), measurements indicative of positions of an eye of a user (referred to herein as "eye positions").

In Step 2, capturing images of the eye by a head-mounted camera (e.g., the head-mounted camera 304). Optionally, a first range of eye positions trackable from the images is narrower than a second range of eye positions trackable from the measurements taken in Step 1.

In Step 3, calculating eye positions based on the measurements taken in Step 1.

In Step 4, reading the images from the head-mounted camera at a first bitrate when the eye positions fall within the first range.

And in Step 5, refraining from reading the images from the head-mounted camera, or reading the images from the head-mounted camera at a second bitrate that is less than half the first bitrate, when the eye positions fall outside the first range.

In one embodiment, the method may optionally include a step of commanding the head-mounted camera to operate in a low-power mode for a longer percent of time while the eye positions fall outside the first range, compared to a percent of time it operates in low-power mode while the eye positions fall within the first range.

In one embodiment, the method may optionally include the following steps: capturing, by a second head-mounted camera, a second set of images of the eye from a different position than the head-mounted camera; and reading the second set of images from the second head-mounted camera at a higher bitrate when the eye positions fall outside the first range compared to when the eye positions fall within the first range.

The eye tracking system illustrated in FIG. 9A may be utilized in some embodiments to calculate pupil features based on the images 305, which are captured by the head-mounted camera 304.

In some embodiments, an eye tracking system includes the head-mounted device 302, which is configured to take measurements 303 indicative of positions of an eye of a user (referred to herein as "eye positions") and the head-mounted camera 304. In these embodiments, the head-mounted camera 304 is better positioned to capture images of the user's pupil when the eye positions fall within a certain range compared to when the eye positions fall outside the certain range. In some examples, the certain range may be the first range mentioned further above, of eye positions that are trackable from the images 305. In one example, the eye positions that fall outside the certain range span at least 20° of the eye's field of view. In another example, the eye positions that fall outside the certain range span at least 40° of the eye's field of view.

The computer 308 may calculate, in some embodiments, pupil features 309 based on images captured by the head-mounted camera 304. Optionally, the pupil features 309 include at least one of: a pupil center location, a pupil contour, a pupil diameter, a glint location, a glint-pupil vector, a Haar-like feature, a result of an ellipse fitting approach, and a result of pupil edge filtering. The aforementioned pupil features are well known in the art, and discussed in the reference Fuhl, Wolfgang, et al. "Pupil detection for head-mounted eye tracking in the wild: an evaluation of the state of the art", Machine Vision and Applications 27.8 (2016): 1275-1288, which is incorporated herein by reference.

The extent to which the pupil features 309 are calculated by the computer 308 can depend on the eye positions (which are calculated based on the measurements 303). In one embodiment, the computer 308 calculates, at a first average rate, pupil features 309 based on images captured by the head-mounted camera 304 when the eye positions fall within the certain range. For example, the computer 308 may calculate the pupil features 309 at the first rate based on the images 305 (when the first range discussed further above is the same as the certain range). Additionally, the computer 308 may refrain altogether from calculating pupil features when the eye positions fall outside of the certain range. Alternatively to refraining from calculating pupil features, the computer 308 may calculate pupil features at a second average rate, which is less than half the first average rate, based on images captured when the eye positions fall outside the certain range. Optionally, the first average is at least ten times the second average rate. In one example, the first average rate is 100 Hz and the second average rate is 5 Hz. In another example, the first average rate is 200 Hz or more and the second average rate is below 20 Hz.

In some embodiments, the computer 308 commands the head-mounted camera 304 to operate in a low-power mode for a longer percent of time while the eye positions fall outside the certain range, compared to a percent of time it operates in the low-power mode while the eye positions fall within the certain range.

In some embodiments, calculating the pupil features 309 based on the measurements 303 is performed at a rate that is at least ten times higher than a rate at which the images 305 are captured by the head-mounted camera 304.

In some embodiments, the second head-mounted camera 306 captures a second set of images of the eye from a different position than the head-mounted camera 304. Optionally, the computer 308 calculates pupil features based on the second set of images at a higher rate when the eye positions fall outside the certain range compared to when the eye positions fall within the certain range. Optionally, the computer 308 commands the second head-mounted camera 306 to operate in a low-power mode for a longer percent of time while the eye positions fall within the certain range, compared to a percent of time it operates in the low-power mode while the eye positions fall outside the certain range.

The following method may be used by some embodiments of systems modeled according to FIG. 8. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking, with a head-mounted device (e.g., the head-mounted device 302), measurements indicative of positions of an eye of a user (referred to herein as "eye positions").

In Step 2, capturing images of the eye by a head-mounted camera (e.g., the head-mounted camera 304).

In Step 3, calculating eye positions based on the measurements taken in Step 1. Optionally, the head-mounted camera used in Step 2 is better positioned to capture images of the user's pupil when the eye positions fall within a certain range compared to when the eye positions fall outside the certain range.

In Step 4, calculating, at a first average rate, pupil features based on images captured when the eye positions fall within the certain range.

And in Step 5, refraining from calculating pupil features, or calculating pupil features at a second average rate that is less than half the first average rate, based on images captured when the eye positions fall outside the certain range.

In one embodiment, calculating of the eye positions based on the measurements in Step 3 is performed at a rate that is at least ten times higher than rate of capturing the images by the head-mounted camera. Optionally, the method also includes a step of commanding the head-mounted camera to operate in a low-power mode for a longer percent of time while the eye positions fall outside the certain range compared to a percent of time it operates in low-power mode while the eye positions fall within the certain range.

In one embodiment, the method also includes the following steps: capturing, by a second head-mounted camera, a second set of images of the eye from a different position than the head-mounted camera, and calculating pupil features based on the second set of images at a higher rate when the eye positions fall outside the certain range compared to when the eye positions fall within the certain range. Optionally, the method also includes the following steps related to power management: commanding the head-mounted camera to operate in a low-power mode for a longer percent of time while the eye positions fall outside the certain range compared to a percent of time it operates in the low-power mode while the eye positions fall within the certain range; and commanding the second head-mounted camera to operate in a low-power mode for a longer percent of time while the eye positions fall within the certain range compared to a percent of time it operates in the low-power mode while the eye positions fall outside the certain range.

Figure 10:
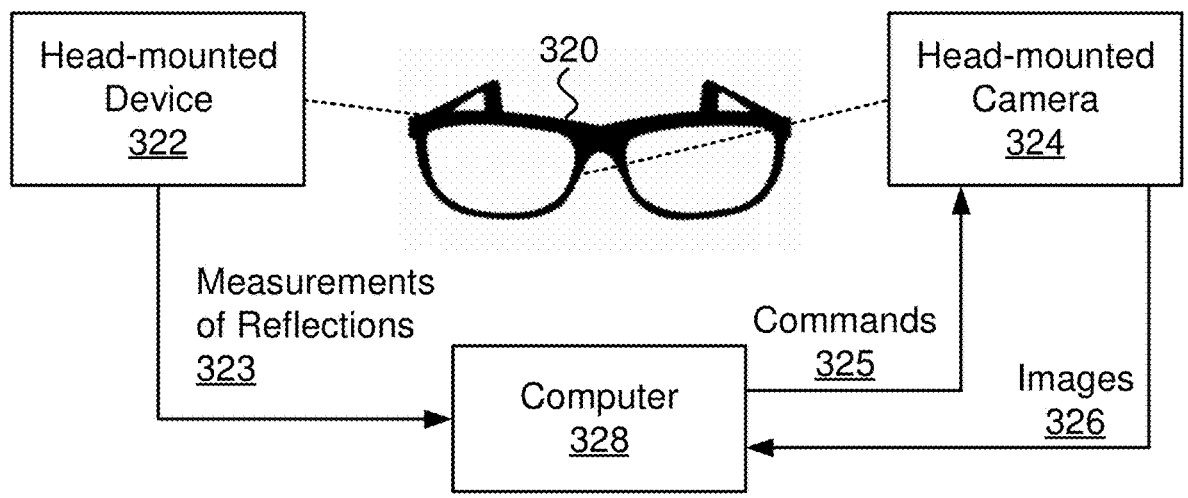
FIG. 10 illustrates an embodiment of an eye tracking system that involves operation of a camera according to eyelid position.

FIG. 10 illustrates an embodiment of an eye tracking system that involves operation of a camera according to eyelid position. In one embodiment, the eye tracking system includes the head-mounted device 322, an inward-facing head-mounted camera 324, and a computer 328. The inward-facing head-mounted camera 324 captures images 326 of an eye. The head-mounted device 322 emits electromagnetic waves towards the eye, and takes measurements 323 of reflections of the electromagnetic waves from the eye. Optionally, an average rate at which the reflections are measured is at least ten times an average rate at which the images 326 are captured.

The head-mounted device 322 may include different types of components in embodiments described herein. These different components may provide different types of signals indicative of the position of the eyelids.

In one embodiment, the head-mounted device 322 includes a photosensor-oculography device (PSOG) that measures reflections of light emitted by the PSOG towards the eye. It is to be noted that the near-infrared (NIR) reflectance of the eyelid is different from the NIR reflectance of the eye, and the NIR reflectance of the eyelashes is different from the NIR reflectance of the skin. Thus, when the head-mounted device 322 includes PSOG, movements of the eyelid change the measured NIR reflections, thus enabling detection of the eyelid position (based on changes to the measured reflections, which are characteristic of the eyelid in different positions).

In another embodiment, the head-mounted device 322 includes an optical flow sensor that measures optical flow and/or visual motion, and the eyelid position is calculated based on an optical flow algorithm. In one example, the optical flow sensor is an image sensor that measures optical flow and/or visual motion, which are affected by the position of the eyelid.

In yet another embodiment, the head-mounted device 322 includes range sensors that measure ranges between the range sensors and the eye. These measurements are affected by the eyelid position, thus enabling detection of the eyelid position (based on changes to the ranges, which are characteristic of the eyelid in different positions).

The computer 328 detects, based on the measurements 323 of the reflections, a position of at least one of the upper and lower eyelids covering the eye (referred to herein as "eyelid position"). The computer 328 operates the head-mounted camera 324 according to the eyelid position in a certain manner, which decreases, in the captured images 326, areas depicting the at least one of the upper and lower eyelids, and optionally increases, in the captured images 326, areas depicting the iris. Optionally, operating the head-mounted camera 324 in the certain manner involves the computer 328 issuing commands 325 to the head-mounted camera 324 based on the eyelid position.

Operating the head-mounted camera 324 in the certain manner, which increases the areas depicting the iris and decreases depiction of the eyelids in the captured images 326, may be done in different ways in embodiments described herein.

In one embodiment, the head-mounted camera 324 utilizes a sensor that supports changing of its region of interest (ROI), similar to the head-mounted camera 274 described herein. In this embodiment, the computer 328 utilizes the eyelid position to set the ROI around a portion of the eye that is not covered by the at least one of upper and lower eyelids. One example of setting the ROI around a portion of the eye that is not covered by the eyelids is to select a rectangle having a height that is a bit longer than the maximum distance between the upper and lower eyelids. In one example, setting the ROI around a portion of the eye that is not covered by the eyelids involves setting the ROI to cover less than half the sensor's field of view. In another example, the computer 328 sets the ROI such that the size of the ROI is proportional to percent of the eyeball uncovered by the eyelid. The proportion may be implemented in steps, such as having 2-6 predefined sizes for the ROI, which depend on the eyelid position. Alternatively, the proportion may be finer, such that the more the at least one of upper and lower eyelids covers the eyeball the smaller the size of the ROI.

Figure 11A:
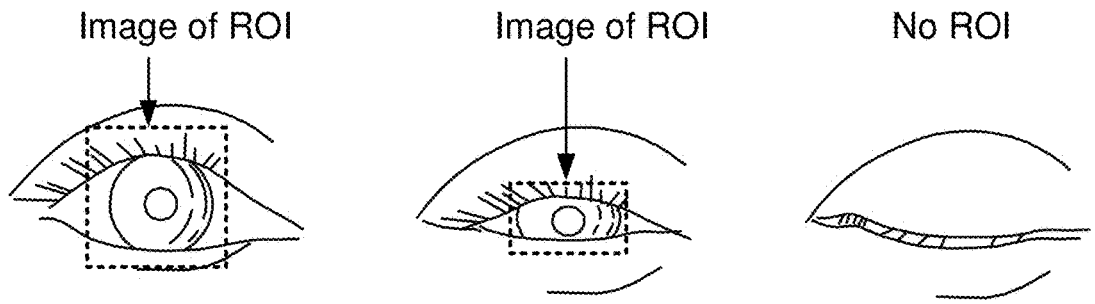
FIG. 11A illustrates different ROIs that are set according to different eyelid positions.

FIG. 11A illustrates different ROIs that are set according to different eyelid positions. The image on the left depicts an open eye in which the ROI is large and includes the full pupil (with a bit of the upper and lower eyelids in the ROI. The middle image depicts a partially closed eye, in which the eyelids cover part of the pupil. The ROI in this image is smaller than the one on the left due to the visible portion of the pupil being smaller The image on the right in FIG. 11A depicts a scenario in which the eye is shut and thus no ROI is set.

Figure 11B:
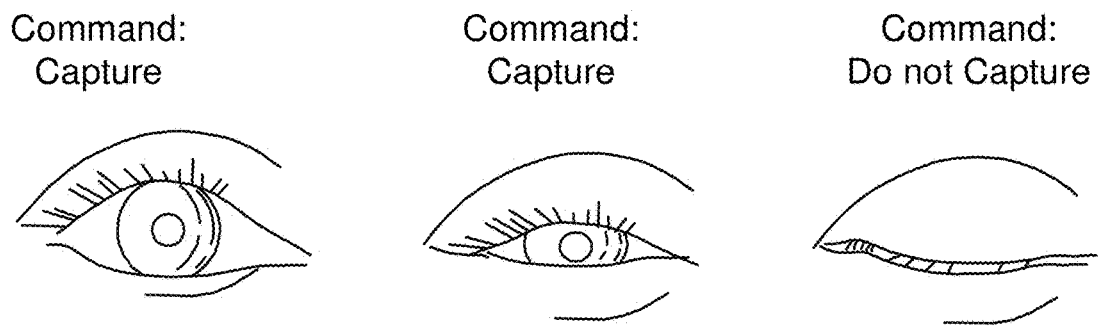
FIG. 11B illustrates selective issuing of commands to capture images based on the extent to which the eye is open.

In another embodiment, in order to operate the head-mounted camera 324 in the certain manner, which increases the areas depicting the iris and decreases depiction of the eyelids in the captured images 326, the computer 328 refrains from commanding the head-mounted camera 324 to capture images during eyeblinks and/or while the eye is closed. This manner of selectively commanding the head-mounted camera 324 is illustrated in FIG. 11B, in which the commands to capture images are issued when the eye is open or partially open (images on the left and center), but no command to capture is issued when the eye is closed (image on the right).

The eyelid position can be indicative of emotional responses of the user. In some embodiments, when the eyelid is determined to be in a certain position and/or it is detected that the eyelid performs a certain movement, it can be advantageous to obtain additional measurements in order to better ascertain the specifics of the user's emotional response occurring at that time. In one example, raising the upper eyelid may indicate an emotional response comprising an expression of surprise, which may be worth monitoring. In this example, the computer 328 detects a raising of the upper eyelid based on the measurements 323 of the reflections, and increases the frame rate of the head-mounted camera 324 during the time the upper eyelid is raised above a threshold. In another example, raising of the lower eyelid may indicate an emotional response comprising an expression of anger, which may be worth monitoring. In this example, the computer 328 detects a raising of the lower eyelid based on the measurements 323 of the reflections, and increases the frame rate of the head-mounted camera 324 during the time the lower eyelid is raised above a threshold. To detect the raising of the upper eyelid and/or the raising of the lower eyelid, the computer 328 may utilize a machine learning-based model, as described in more detail below.

Various embodiments described herein involve detecting the eyelid position (of the top eyelid and/or the bottom eyelid) based on measurements 323 of the reflections, and then utilizing the eyelid position to determine operational parameters, such as issuing the commands 325 to determine how the head-mounted camera 324 should operate. In some embodiments, the eyelid position can often more easily and/or accurately be determined from images (e.g., images taken by the head-mounted camera 324), using image analysis techniques known in the art. However, as explained below, by using such images to train a machine learning-based model, it is possible to determine the eyelid position, even at times at which images are not captured by the head-mounted camera 324, which can help conserve power.

In some embodiments, measurements of the reflections obtained by the head-mounted device 322 are used to detect the eyelid position by calculating, based on the measurements of the reflections, a value indicative of the eyelid position. The calculation of the value indicative of the eyelid position may utilize, in these embodiments, a model that is trained with samples that each includes feature values that are generated based on measurements of reflections (measured by the head-mounted device 322) and a label generated from analysis of one or more images captured by a certain camera at the same time the measurements used to generate the feature values were taken. In one example, the certain camera may be the head-mounted camera 324. In another example, the certain camera may be a non-head-mounted device, such as a camera of a cellphone, webcam, laptop, or some other non-head-mounted camera. Examples of the feature values that may be generated by the computer 328 include values indicating the level of electromagnetic waves emitted towards the eye and the extent of reflections.

In one example, in which the head-mounted device 322 includes PSOG at least some of the feature values may include various PSOG-related feature values that are known in the art mentioned in references described herein. In another example, at least some of the feature values may include values indicative of the extent of optical flow and/or changes to the extent of optical flow, which are known in the art, as discussed in Jiménez-Pinto, et al., "Optical flow and driver's kinematics analysis for state of alert sensing." *Sensors* 13.4 (2013): 4225-4257 and in Cho, et al., "Moving object detection based on optical flow estimation and a Gaussian mixture model for advanced driver assistance systems", in *Sensors* 19.14 (2019): 3217. In yet another example, in which the head-mounted device 322 includes range sensors, at least some the feature values are indicative of the ranges measured between the ranges sensors and the eye.

The labels used for the training samples may be generated using image analysis techniques known in the art for determining positions of eyelids. Training samples that include the aforementioned feature values and labels are provided to a machine learning algorithm, such as an algorithm for training a regression model, a neural network, etc. This results in a personalized model that is capable of detecting the eyelid position of the user based on measurements of the user obtained with the head-mounted device 322.

In one example, the computer 328 extracts eyelid positions by analyzing the images 326 (referred to herein as "image-based positions"), and utilizes the image-based positions and the measurements 323 of the reflections to generate labeled training samples for training a machine learning-based model for detecting the eyelid position based on additional measurements of reflections taken with the head-mounted device 322.

In another example, the computer 328 receives photos from a camera belonging to a non-head-mounted device, extracts eyelid positions by analyzing the photos (referred to herein as "photo-based positions"), and utilizes the photo-based positions and the measurements 323 of the reflections to generate labeled training samples for training a machine learning-based model for detecting the eyelid position based on additional measurements of reflections taken with the head-mounted device 322. In this example, the computer 328 may include a head-mounted computer and a non-head-mounted computer that are configured to communicate over a wireless communication channel, the non-head-mounted computer is used to train the model, and the head-mounted computer may use the trained model for detecting the eyelid position based on measurements of the reflections measured by the head-mounted device 322.

In one embodiment, the computer 328 calculates a level of tiredness of the user based on the eyelid position, and adjusts a frequency at which the images 326 are captured based on the level of tiredness. The level of tiredness can be used in various applications. For example, while using an entertainment application, the computer 328 may reduce the frequency at which the images 326 are captured as the user becomes more tired because it may be assumed that the user's responses become slower. In another example, while using a driver safety application, the computer 328 may increase the frequency at which the images are captured as the user becomes more tired.

Detecting a level of tiredness may be done utilizing a machine learning-based model, which is provided feature values generated based on data that includes indications of the eyelid position (and possibly other data indicative of the physiological state of the user and/or the activity level of the user). The computer 328 may then utilize a certain model to calculate, based on the feature values, a value indicative of the tiredness level of the user. The certain model, in this embodiment, may be trained with training samples, each including: (i) feature values generated based on measurements of a certain user at a certain time (which include an indication of the eyelid position at the certain time and possibly other data indicative of the physiological state of the certain user and/or the activity level of the certain user at the certain time), and (ii) a label indicative of the tiredness level of the certain user at the certain time. Some examples of feature values that may be determined based on the eyelid position include average rate/duration of number of blinks, average height of the eyelid, average area of the eye that is exposed, etc. The tiredness level values of the certain user (which are used in the training) may be determined in various ways, such as a self-report by the certain user, or analysis of images of the certain user using image analysis methods known in the art of detecting the level of tiredness.

The following method may be used by some embodiments of systems modeled according to FIG. 10. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, capturing images of an eye by an inward-facing head-mounted camera (e.g., the head-mounted camera 324).

In Step 2, emitting, by a head-mounted device (e.g., the head-mounted device 322), electromagnetic waves towards the eye, and taking measurements of reflections of the electromagnetic waves from the eye (e.g., by the head-mounted device 322). Optionally, an average rate of taking measurements of the reflections in this step is at least ten times average rate of capturing the images in Step 1.

In Step 3, detecting, based on the measurements of the reflections, a position of at least one of the upper and lower eyelids covering the eye (referred to herein as the "eyelid position").

And in Step 4, operating the inward-facing head-mounted camera according to the eyelid position in a manner that (i) increases, in the captured images, areas depicting the iris, and (ii) decreases, in the captured images, areas depicting the at least one of the upper and lower eyelids.

In one embodiment, the inward-facing head-mounted camera utilizes a sensor that supports changing of its region of interest (ROI), and operating the inward-facing head-mounted camera in the manner described in Step 4 involves utilizing the eyelid position to set the ROI around a portion of the eye that is not covered by the at least one of upper and lower eyelids.

In one embodiment, the method optionally includes a step involving calculating a level of tiredness based on the eyelid position, and adjusting a frequency at which the images are captured in Step 1 based on the level of tiredness.

In one embodiment, the method optionally includes performing the following steps to train a machine learning-based model that is used for detecting the eyelid position based on additional measurements of reflections (of electromagnetic waves from the eye): extracting eyelid positions by analyzing the images (referred to herein as "image-based positions"); generating labels based on the image-based positions; generating feature values based on the measurements of the reflections; and providing the labels and feature values to train the machine learning-based model for detecting the eyelid position based on the additional measurements of the reflections. Optionally, the machine learning-based model is used to detect the eyelid position at future times during which images of the eye were not captured.

In one embodiment, the method optionally includes performing the following steps to train a machine learning-based model that is used for detecting the eyelid position based on additional measurements of reflections (of electromagnetic waves from the eye): receiving photos from a camera belonging to a non-head-mounted device, extracting eyelid positions by analyzing the photos (referred to herein as "photo-based positions"), generating labels based on the photo-based positions, generating feature values based on the measurements of the reflections, and providing the labels and feature values to train the machine learning-based model for detecting the eyelid position based on the additional measurements of the reflections. Optionally, the machine learning-based model is used to detect the eyelid position at future times during which images of the eye were not captured.

US Patent Application 2019/0223737A1, which is herein incorporated by reference in its entirety and is a previous patent application of the Applicant of this invention, discusses and illustrates in paragraphs 0040-0049, together with their associated drawings, various examples of head-mounted systems equipped with head-mounted cameras, which can be adapted to be utilized with some of the embodiments herein. For example, these paragraphs illustrate various inward-facing head-mounted cameras coupled to an eyeglasses frame, illustrate cameras that capture regions on the periorbital areas, illustrate an optional computer that may include a processor, memory, a battery and/or a communication module, illustrate inward-facing head-mounted cameras coupled to an augmented reality devices, illustrate head-mounted cameras coupled to a virtual reality device, illustrate head-mounted cameras coupled to a sunglasses frame, illustrate cameras configured to capture various regions, such as the forehead, the upper lip, the cheeks, and sides of the nose, illustrate inward-facing head-mounted cameras mounted to protruding arms, illustrate various inward-facing head-mounted cameras having multi-pixel sensors (FPA sensors) configured to capture various regions, illustrate head-mounted cameras that are physically coupled to a frame using a clip-on device configured to be attached/detached from a pair of eyeglasses in order to secure/release the device to/from the eyeglasses, illustrate a clip-on device holds at least an inward-facing camera, a processor, a battery, and a wireless communication module, illustrate right and left clip-on devices configured to be attached behind an eyeglasses frame, illustrate a single-unit clip-on device configured to be attached behind an eyeglasses frame, and illustrate right and left clip-on devices configured to be attached/detached from an eyeglasses frame and having protruding arms to hold the inward-facing head-mounted cameras.

It is noted that the elliptic and other shapes of the regions captured by cameras and other sensing devices (such as PSOG) in some of the drawings are just for illustration purposes, and the actual shapes of the regions are usually not as illustrated. Furthermore, illustrations and discussions of a camera represent one or more cameras, where each camera may have the same field of view (FOV) and/or different FOVs. A camera includes multiple sensing elements, and the illustrated region captured by the camera usually refers to the total region captured by the camera, which is made of multiple regions that are respectively captured by the different sensing elements. The positions of the cameras in the figures are just for illustration, and the cameras may be placed at other positions.

Various embodiments described herein involve a head-mounted system (HMS) that may be connected, using wires and/or wirelessly, with a device carried by the user and/or a non-wearable device. The HMS may include a battery, a computer, sensors, and a transceiver.

Figure 12A:
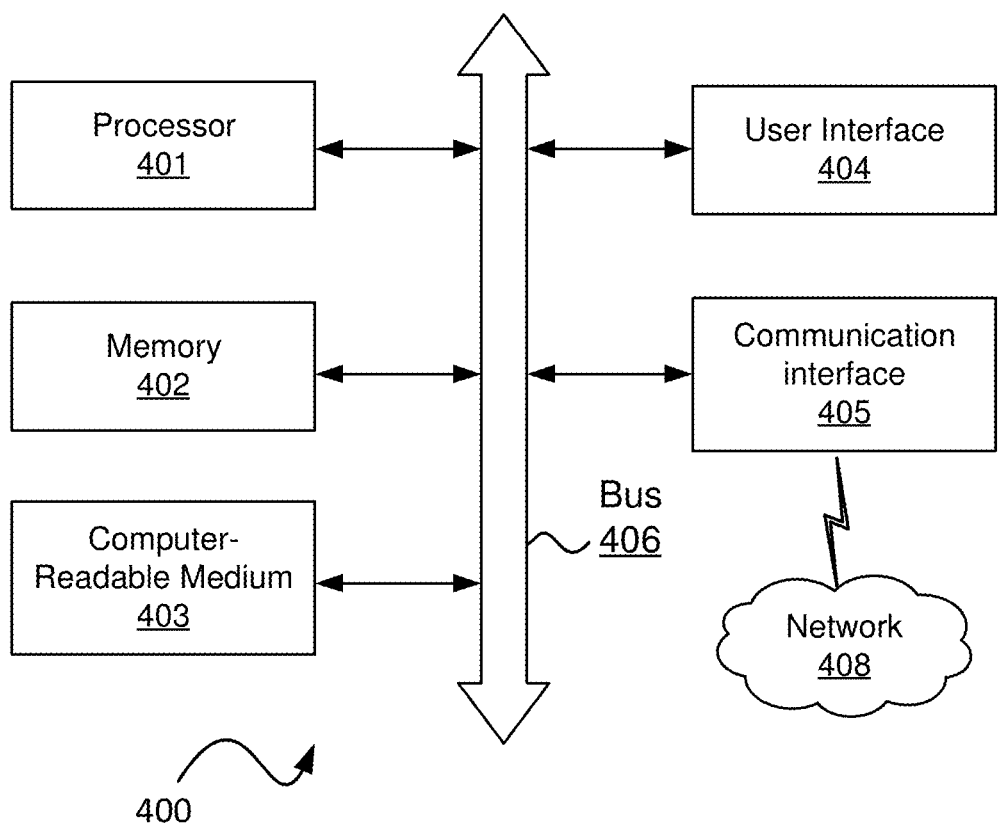
FIG. 12A and FIG. 12B are schematic illustrations of possible embodiments for computers.
Figure 12B:
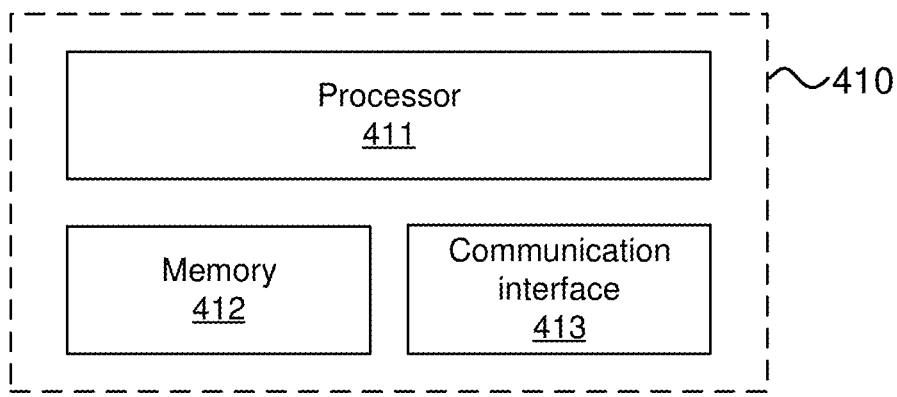

FIG. 12A and FIG. 12B are schematic illustrations of possible embodiments for computers (400, 410) that are able to realize one or more of the embodiments discussed herein that include a "computer". The computer (400, 410) may be implemented in various ways, such as, but not limited to, a microcontroller, a computer on a chip, a system-on-chip (SoC), a system-on-module (SoM), a processor with its required peripherals, a server computer, and/or any other computer form capable of executing a set of computer instructions. Further, references to a computer or a processor include any collection of one or more computers and/or processors (which may be at different locations) that individually or jointly execute one or more sets of computer instructions. This means that the singular term "computer" is intended to imply one or more computers, which jointly perform the functions attributed to "the computer". In particular, some functions attributed to the computer may be performed by a computer on a wearable device (e.g., smartglasses) and/or a computer of the user (e.g., smartphone), while other functions may be performed on a remote computer, such as a cloud-based server.

The computer 400 includes one or more of the following components: processor 401, memory 402, computer readable medium 403, user interface 404, communication interface 405, and bus 406. The computer 410 includes one or more of the following components: processor 411, memory 412, and communication interface 413.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, and/or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium. In one example, the computer-readable medium 403 may include one or more of the following: RAM, ROM, EEPROM, optical storage, magnetic storage, biologic storage, flash memory, or any other medium that can store computer readable data.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non-transitory computer-readable medium, and may be updated and/or downloaded via a communication network, such as the Internet. Optionally, the computer program may be downloaded from a central repository, such as Apple App Store and/or Google Play. Optionally, the computer program may be downloaded from a repository, such as an open source and/or community run repository (e.g., GitHub).

At least some of the methods described herein are "computer-implemented methods" that are implemented on a computer, such as the computer (400, 410), by executing instructions on the processor (401, 411). Additionally, at least some of these instructions may be stored on a non-transitory computer-readable medium.

As used herein, references to "one embodiment" (and its variations) mean that the feature being referred to may be included in at least one embodiment of the invention. Separate references to embodiments may refer to the same embodiment, may illustrate different aspects of an embodiment, and/or may refer to different embodiments.

Sentences in the form of "X is indicative of Y" mean that X includes information correlated with Y, up to the case where X equals Y. Sentences in the form of "provide/receive an indication (of whether X happened)" may refer to any indication method.

The word "most" of something is defined as above 51% of the something (including 100% of the something). Both a "portion" of something and a "region" of something refer to a value between a fraction of the something and 100% of the something The word "region" refers to an open-ended claim language, and a camera said to capture a specific region on the face may capture just a small part of the specific region, the entire specific region, and/or a portion of the specific region together with additional region(s). The phrase "based on" indicates an open-ended claim language, and is to be interpreted as "based, at least in part, on". Additionally, stating that a value is calculated "based on X" and following that, in a certain embodiment, that the value is calculated "also based on Y", means that in the certain embodiment, the value is calculated based on X and Y. Variations of the terms "utilize" and "use" indicate an open-ended claim language, such that sentences in the form of "detecting X utilizing Y" are intended to mean "detecting X utilizing at least Y", and sentences in the form of "use X to calculate Y" are intended to mean "calculate Y based on X".

The terms "first", "second" and so forth are to be interpreted merely as ordinal designations, and shall not be limited in themselves. A predetermined value is a fixed value and/or a value determined any time before performing a calculation that utilizes the predetermined value. When appropriate, the word "value" may indicate a "predetermined value". The word "threshold" indicates a "predetermined threshold", which means that the value of the threshold, and/or the logic used to determine whether the threshold is reached, is known before start performing computations to determine whether the threshold is reached.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

We claim:

1. An eye tracking system configured to operate a camera according to eyelid position, comprising:
   an inward-facing head-mounted camera configured to capture images of an eye;
   a head-mounted device configured to emit electromagnetic waves towards the eye, and to take measurements of reflections of the electromagnetic waves from the eye; wherein an average rate at which the measurements of the reflections are taken is higher than an average rate at which the images are captured; and
   a computer configured to:
   detect, based on the measurements of the reflections, a position of at least one of the eyelids covering the eye (eyelid position); and
   operate the inward-facing head-mounted camera according to the eyelid position in a manner that decreases, in the captured images, areas depicting the at least one of the eyelids.

2. The eye tracking system of claim 1, wherein the inward-facing head-mounted camera utilizes a sensor that supports changing of its region of interest (ROI), and the computer is further configured to utilize the eyelid position to set the ROI around a portion of the eye that is not covered by the at least one of the eyelids.

3. The eye tracking system of claim 2, wherein the ROI covers less than half the sensor's field of view, and wherein the average rate at which the measurements of the reflections are taken is at least ten times the average rate at which the images are captured.

4. The eye tracking system of claim 2, wherein the computer is configured to set the ROI such that the size of the ROI is proportional to area of the eyeball uncovered by the eyelid.

5. The eye tracking system of claim 2, wherein the computer is further configured to operate the inward-facing head-mounted camera according to the eyelid position in a manner that increases, in the captured images, areas depicting the iris.

6. The eye tracking system of claim 2, wherein the computer is further configured to detect a raising of the upper eyelid based on the measurements of the reflections, and to increase a frame rate of the inward-facing head-mounted camera during the time the upper eyelid is raised above a threshold; whereby raising of the upper eyelid may indicate an emotional response comprising an expression of surprise.

7. The eye tracking system of claim 2, wherein the computer is further configured to detect a raising of the lower eyelid based on the measurements of the reflections, and to increase a frame rate of the inward-facing head-mounted camera during the time the lower eyelid is raised above a threshold; whereby raising of the lower eyelid may indicate an emotional response comprising an expression of anger.

8. The eye tracking system of claim 1, wherein in order to operate the inward-facing head-mounted camera according to the eyelid position the computer is configured to refrain from commanding the camera to capture the images during blinks and/or while the eye is closed.

9. The eye tracking system of claim 1, wherein the computer is further configured to: extract eyelid positions by analyzing the images (image-based positions), and utilize the image-based positions and the measurements of the reflections to generate labeled training samples for training a machine learning-based model for detecting the eyelid position based on additional measurements of reflections taken with the head-mounted device.

10. The eye tracking system of claim 1, wherein the computer is further configured to: receive photos from a camera belonging to a non-head-mounted device, extract eyelid positions by analyzing the photos (photo-based positions), and utilize the photo-based positions and the measurements of the reflections to generate labeled training samples for training a machine learning-based model for detecting the eyelid position based on additional measurements of reflections taken with the head-mounted device.

11. The eye tracking system of claim 10, wherein the computer comprises a head-mounted computer and a non-head-mounted computer that are configured to communicate over a wireless communication channel; the non-head-mounted computer is configured to train the model, and the head-mounted computer is configured to use the trained model for detecting the eyelid position based on reflections.

12. The eye tracking system of claim 1, wherein the head-mounted device comprises a photosensor-oculography device (PSOG) configured to measure reflections of light emitted by the PSOG towards the eye.

13. The eye tracking system of claim 1, wherein the head-mounted device comprises an optical flow sensor configured to measure optical flow and/or visual motion, and the eyelid position is calculated based on an optical flow algorithm.

14. The eye tracking system of claim 1, wherein the head-mounted device comprises range sensors configured to measure ranges between the range sensors and the eye; whereby measurements of the range sensors are affected by the eyelid position.

15. A method comprising:
   capturing images of an eye by an inward-facing head-mounted camera;
   emitting, by a head-mounted device, electromagnetic waves towards the eye, and taking measurements of reflections of the electromagnetic waves from the eye;
   wherein average rate of taking measurements of the reflections is higher than average rate of capturing the images;
   detecting, based on the measurements of the reflections, a position of at least one of the eyelids covering the eye (eyelid position); and
   operating the inward-facing head-mounted camera according to the eyelid position in a manner that decreases, in the captured images, areas depicting the at least one of the eyelids.

16. The method of claim 15, wherein the inward-facing head-mounted camera utilizes a sensor that supports changing of its region of interest (ROI), and further comprising utilizing the eyelid position to set the ROI around a portion of the eye that is not covered by the at least one of the eyelids.

17. The method of claim 15, further comprising operating the inward-facing head-mounted camera according to the eyelid position in a manner that increases, in the captured images, areas depicting the iris; and wherein the average rate of taking measurements of the reflections is at least ten times the average rate of capturing the images.

18. The method of claim 15, further comprising performing the following steps to train a machine learning-based model that is used for detecting the eyelid position based on additional measurements of reflections: extracting eyelid positions by analyzing the images (image-based positions); generating labels based on the image-based positions; generating feature values based on the measurements of the reflections; and providing the labels and feature values to train the machine learning-based model for detecting the eyelid position based on the additional measurements of the reflections.

19. The method of claim 15, further comprising performing the following steps to train a machine learning-based model that is used for detecting the eyelid position based on additional measurements of reflections: receiving photos from a camera belonging to a non-head-mounted device, extracting eyelid positions by analyzing the photos (photo-based positions), generating labels based on the photo-based positions, generating feature values based on the measurements of the reflections, and providing the labels and feature values to train the machine learning-based model for detecting the eyelid position based on the additional measurements of the reflections.

20. A non-transitory computer readable medium storing one or more computer programs configured to cause a processor-based system to execute steps comprising:
   capturing images of an eye by an inward-facing head-mounted camera;
   emitting, by a head-mounted device, electromagnetic waves towards the eye, and taking measurements of reflections of the electromagnetic waves from the eye;
   wherein average rate of taking measurements of the reflections is higher than average rate of capturing the images;
   detecting, based on the measurements of the reflections, a position of at least one of the eyelids covering the eye (eyelid position); and
   operating the inward-facing head-mounted camera according to the eyelid position in a manner that decreases, in the captured images, areas depicting the at least one of the eyelids.

* * * * *